(12) United States Patent
Duhamel et al.

(10) Patent No.: US 10,737,007 B2
(45) Date of Patent: Aug. 11, 2020

(54) PATIENT ADAPTER FOR DRIVELINE CABLE AND METHODS

(71) Applicant: TC1 LLC, St. Paul, MN (US)

(72) Inventors: Julien Duhamel, Billerica, MA (US); John Mark Di Paola, Livermore, CA (US); Dustin Roelle, Mountain House, CA (US); Dmitry Protsenko, Vallejo, CA (US)

(73) Assignee: TC1 LLC, St. Paul, MN (US)

( * ) Notice: Subject to any disclaimer, the term of this patent is extended or adjusted under 35 U.S.C. 154(b) by 281 days.

(21) Appl. No.: 15/966,869

(22) Filed: Apr. 30, 2018

(65) Prior Publication Data

US 2018/0311427 A1 Nov. 1, 2018

Related U.S. Application Data

(60) Provisional application No. 62/491,612, filed on Apr. 28, 2017.

(51) Int. Cl.
*A61M 1/12* (2006.01)
*H01B 7/04* (2006.01)
*A61M 1/10* (2006.01)

(52) U.S. Cl.
CPC ............ *A61M 1/122* (2014.02); *A61M 1/127* (2013.01); *H01B 7/048* (2013.01); *A61M 1/101* (2013.01); *A61M 2205/04* (2013.01)

(58) Field of Classification Search
None
See application file for complete search history.

(56) References Cited

U.S. PATENT DOCUMENTS

| | | |
|---|---|---|
| 5,695,471 A | 12/1997 | Wampler |
| 5,708,346 A | 1/1998 | Schob |
| 5,888,242 A | 3/1999 | Antaki et al. |
| 5,904,646 A * | 5/1999 | Jarvik ............... A61M 39/0247 600/16 |
| 6,053,705 A | 4/2000 | Schob et al. |
| 6,071,093 A | 6/2000 | Hart |
| 6,100,618 A | 8/2000 | Schoeb et al. |
| 6,116,862 A | 9/2000 | Rau et al. |

(Continued)

FOREIGN PATENT DOCUMENTS

WO 2010025411 A2 3/2010

*Primary Examiner* — Kennedy Schaetzle
(74) *Attorney, Agent, or Firm* — Kilpatrick Townsend & Stockton LLP

(57) ABSTRACT

A patient adapter for connecting a driveline cable between an implantable blood pump and a controller. The patient adapter provides a sufficiently large form factor to make connecting ends of a driveline cable easy for patients who lack dexterity or have unclear vision. The patient adapter includes an adapter body that defines a central lumen that extends through an entire length of the adapter body. The central lumen is configured to receive an end of a percutaneous end connector of the driveline cable and an end of a controller end connector of the driveline cable. The patient adapter includes a first mating feature configured to engage a corresponding feature of the percutaneous end connector and a second mating feature configured to engage a corresponding feature of the controller end connector. A thickness of the adapter body is greatest at a position proximate the controller end connector.

23 Claims, 20 Drawing Sheets

(56) References Cited

U.S. PATENT DOCUMENTS

| | | |
|---|---|---|
| 6,186,665 B1 | 2/2001 | Maher et al. |
| 6,222,290 B1 | 4/2001 | Schob et al. |
| 6,234,772 B1 | 5/2001 | Wampler et al. |
| 6,249,067 B1 | 6/2001 | Schob et al. |
| 6,264,635 B1 | 7/2001 | Wampler et al. |
| 6,278,251 B1 | 8/2001 | Schob |
| 6,351,048 B1 | 2/2002 | Schob et al. |
| 6,355,998 B1 | 3/2002 | Schob et al. |
| 6,634,224 B1 | 10/2003 | Schob et al. |
| 6,688,861 B2 | 2/2004 | Wampler |
| 6,879,074 B2 | 4/2005 | Amrhein et al. |
| 6,991,595 B2 | 1/2006 | Burke et al. |
| 7,112,903 B1 | 9/2006 | Schob |
| 7,699,586 B2 | 4/2010 | LaRose et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,152,493 B2 | 4/2012 | LaRose et al. |
| 8,323,174 B2 | 12/2012 | Jeevanandam et al. |
| 8,449,444 B2 | 5/2013 | Poirier |
| 8,506,471 B2 | 8/2013 | Bourque |
| 8,562,508 B2 | 10/2013 | Dague et al. |
| 8,597,350 B2 | 12/2013 | Rudser et al. |
| 8,652,024 B1 * | 2/2014 | Yanai ................. A61M 39/1011 600/16 |
| 8,657,733 B2 | 2/2014 | Ayre et al. |
| 8,668,473 B2 | 3/2014 | Larose et al. |
| 8,794,989 B2 | 8/2014 | Kearsley et al. |
| 10,279,093 B2 * | 5/2019 | Reichenbach ............ A61F 2/07 |
| 10,483,690 B1 * | 11/2019 | Stanfield ............ H01R 13/6272 |
| 2005/0071001 A1 | 3/2005 | Jarvik |
| 2005/0137614 A1 * | 6/2005 | Porter .................... A61B 17/11 606/153 |
| 2007/0078293 A1 | 4/2007 | Shambaugh et al. |
| 2007/0208290 A1 * | 9/2007 | Pecor ................. A61M 39/1011 604/4.01 |
| 2008/0021394 A1 | 1/2008 | Larose et al. |
| 2009/0203957 A1 | 8/2009 | Larose et al. |
| 2011/0298304 A1 * | 12/2011 | Cotter ................... A61M 1/127 307/147 |
| 2012/0046514 A1 | 2/2012 | Bourque |
| 2012/0095281 A1 | 4/2012 | Reichenbach et al. |
| 2012/0149229 A1 * | 6/2012 | Kearsley ............... A61M 1/127 439/339 |
| 2013/0096364 A1 | 4/2013 | Reichenbach et al. |
| 2013/0121821 A1 | 5/2013 | Ozaki et al. |
| 2013/0127253 A1 | 5/2013 | Stark et al. |
| 2013/0170970 A1 | 7/2013 | Ozaki et al. |
| 2013/0225909 A1 | 8/2013 | Dormanen et al. |
| 2013/0314047 A1 | 11/2013 | Eagle et al. |
| 2014/0094645 A1 * | 4/2014 | Lafontaine .......... A61M 1/1008 600/16 |
| 2015/0290377 A1 * | 10/2015 | Kearsley ........... A61M 39/0208 49/465 |
| 2016/0030652 A1 * | 2/2016 | Arndt ...................... A61M 1/10 600/16 |
| 2016/0367819 A1 * | 12/2016 | Eldridge .............. A61N 1/3752 |
| 2017/0324185 A1 * | 11/2017 | Hodges ................ A61M 1/101 |
| 2017/0354772 A1 * | 12/2017 | Tajima ................ A61M 1/1008 |
| 2018/0055983 A1 * | 3/2018 | Bourque .............. A61M 1/127 |
| 2019/0290820 A1 * | 9/2019 | Nguyen ................ A61M 1/122 |
| 2020/0069855 A1 * | 3/2020 | Matthes ............. A61M 1/1086 |

* cited by examiner

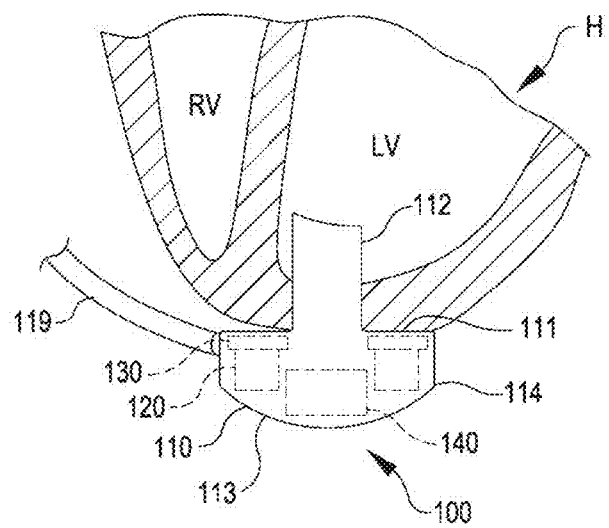
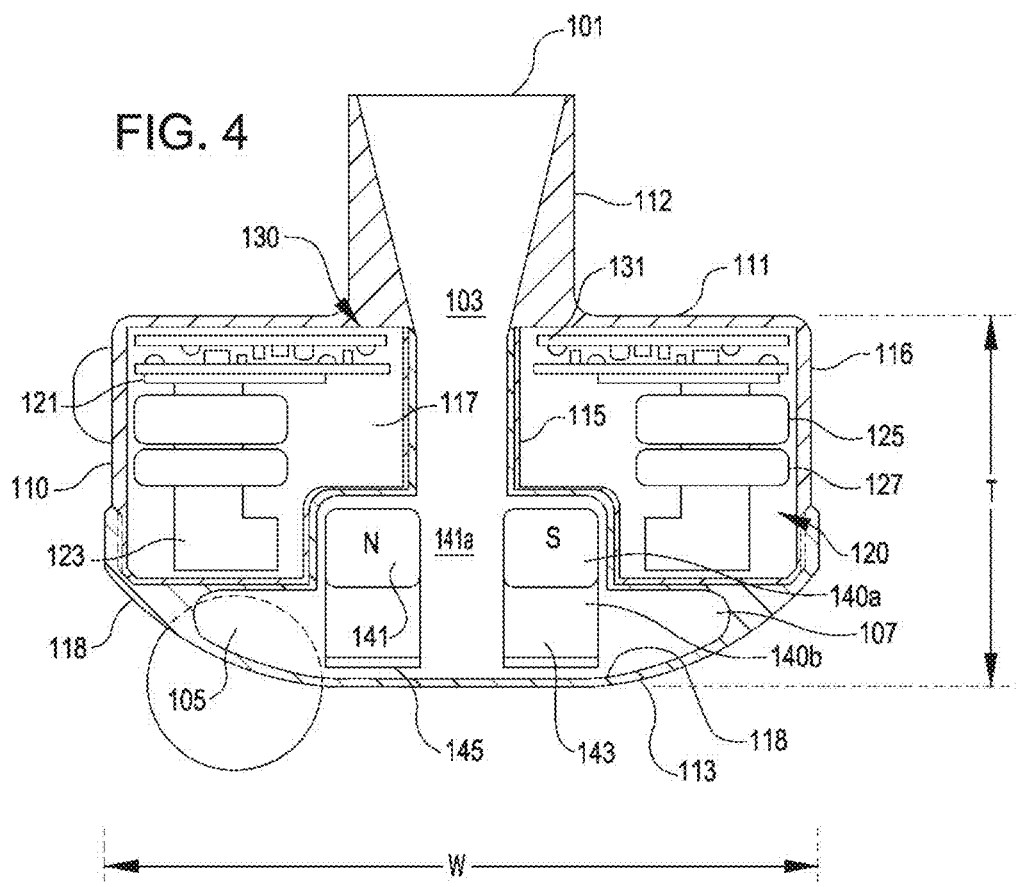

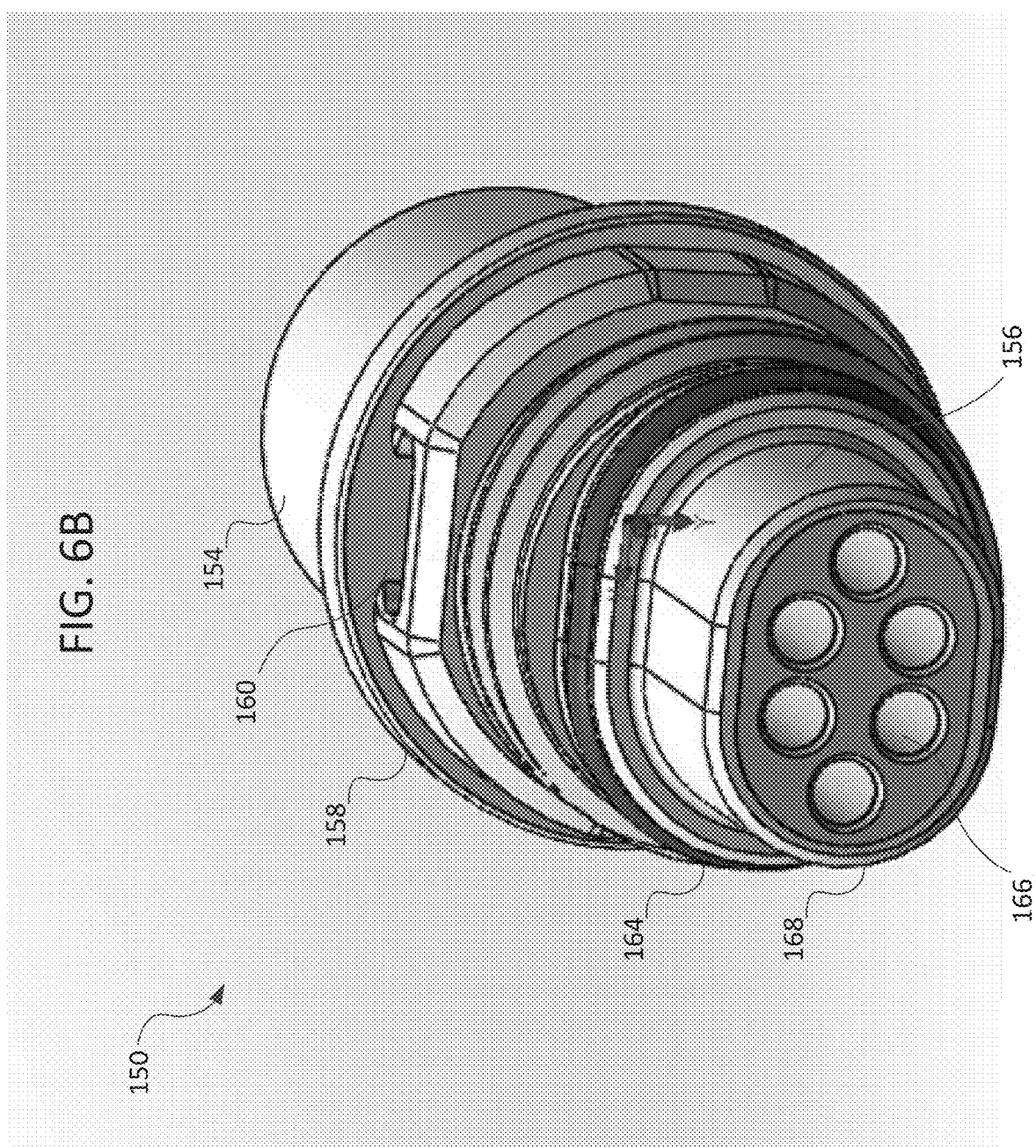

PATIENT ADAPTER FOR DRIVELINE CABLE AND METHODS

CROSS-REFERENCE TO RELATED APPLICATIONS

The present application claims the benefit of U.S. Provisional Application Ser. No. 62/491,612, filed on Apr. 28, 2017, which is incorporated by reference herein in its entirety for all purposes.

BACKGROUND

This application relates generally to mechanical circulatory support systems, and more specifically relates to a patient adapter for a driveline cable of an implantable blood pump.

Implantable blood pumps, such as ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

The VAD is powered and may also be controlled by a driveline cable that extends from the VAD and exits through an aperture of the patient to an external power source and/or controller device. The driveline cable terminates in a connector adapted to connect to a corresponding connector receptacle of an external power source/control unit worn by the patient. The connector includes a group of electrical contacts that electrically engage with a corresponding group of electrical contacts within the receptacle when connected.

During implantation of the VAD, a connector of an associated driveline cable used to power and control the device may be exposed to fluids, such as saline, blood, or other fluids, or debris which may damage or degrade its internal components. In some devices, after implantation of the VAD, the connector may periodically be detached from the power source by the patient for various purposes, for example when the patient showers or bathes. Given that may of the patients utilizing such a device are elderly and may not have high dexterity or clear vision, it is desirable to make the connector easy to manipulate for simple connection and/or disconnection of the driveline cable. It would be further desirable to minimize an incision opening in the patient's abdomen necessary to couple the connector with the VAD. As such, it may be advantageous to provide improved connector assemblies for a driveline cable of an implantable blood pump.

BRIEF SUMMARY OF THE INVENTION

The present invention provides a patient-friendly driveline cable connection. More specifically, the invention provides a patient adapter that increases a form factor from a percutaneous portion to an exterior patient side. This allows a small percutaneous portion of the driveline cable assembly to be coupled with an implantable blood pump and bored through the patient's abdominal wall. The resultant aperture or hole in the patient's abdomen should be as small as possible to promote quick healing and to prevent infection. However, most patient's using such blood pumps cannot manipulate connectors that are sized to match a desired small bore size. Advantageously, a patient adapter may be coupled to the small percutaneous portion by surgical staff. The patient adapter may be of a sufficiently large form factor so as to be easily manageable for most patients, and particularly those who lack dexterity and/or clear vision. A controller end connector may then be coupled to the patient adapter to complete a power and/or control circuit between the controller and the implantable blood pump.

In one embodiment, a patient adapter for connecting a driveline cable between an implantable blood pump and a controller is provided. The patient adapter may include an adapter body that defines a central lumen that extends through an entire length of the adapter body. The central lumen may be configured to receive an end of a percutaneous end connector of the driveline cable and an end of a controller end connector of the driveline cable. The patient adapter may include a first mating feature configured to engage a corresponding feature of the percutaneous end connector and a second mating feature configured to engage a corresponding feature of the controller end connector. A thickness of the adapter body may be greatest at a position proximate the controller end connector.

In some embodiments, the first mating feature may include a cantilever snap-fit arm having a protrusion. The corresponding mating feature of the percutaneous end connector may define a recess configured to receive and secure the protrusion. In some embodiments, the corresponding feature of the controller end connector may include a cantilever snap-fit arm having a protrusion. The second mating feature may define a recess having a distal side that is configured to contact a proximal side of the of the protrusion. The distal side may extend inward from an outer surface of the adapter body at an angle no greater than 90°. In some embodiments, the adapter body has a maximum thickness of at most about 0.5 inches. In some embodiments, the first mating feature and the second mating feature may be positioned on different, adjacent sides of the adapter body. In some embodiments, a width of the adapter body is greater than a height of the adapter body. Although described in terms of a snap-fit connector, one will appreciate from the description herein that other types of connectors may be useful in accordance with the invention.

In another embodiment, a patient adapter for connecting a driveline cable between an implantable blood pump and a controller may include an adapter body that defines a central lumen that extends through an entire length of the adapter body. The adapter body may include a percutaneous section positioned at a first end of the adapter body. A first portion of the central lumen that is positioned within the percutaneous section may be configured to receive a percutaneous end connector of an interior driveline cable. The percutaneous section may include a first mating feature that is configured to engage a corresponding feature of the percutaneous end connector so as to secure the percutaneous end connector with the patient adapter. The adapter body may also include a controller section positioned at a second end of the adapter body. A second portion of the central lumen that is positioned within the controller section may be configured to receive a controller end connector of an exterior driveline cable. The controller section may include a second mating feature configured to releasably engage a corresponding feature of the controller end connector so as to secure the controller end connector with the patient adapter such that the controller end connector is electrically coupleable with the percutaneous end connector within the central lumen. The controller section may have a greater form factor than the percutaneous section. In one example, the controller section has a larger diameter relative to the percutaneous section. In this manner, the user can more easily manipulate the controller section while the percutaneous section remains relatively small and thereby reduces clinical risks (e.g., infection and bleeding).

In some embodiments, the portion of the central lumen that is positioned within the percutaneous section may have a diameter of less than about 0.5 inches and the controller section may have a thickness of at least about 0.75 inches. In some embodiments, the form factor of the controller section is defined by an outer periphery of the controller section and the form factor of the percutaneous section is defined by an outer periphery of the controller section. The outer periphery of the controller section may have at least one major dimension that is at least 0.75 inches. Such dimensions ensure that the controller section of the patient adapter has a sufficiently large form factor so as to be easily handled by patients that lack dexterity and/or clear vision. In some embodiments, the controller section has a different peripheral shape than the percutaneous section to enable manipulation by a user. The controller section may have a shape to enable easier manipulation. For example, the controller section may have flat sides (e.g., polygonal cross-section) and/or gripping surfaces. The ends of the controller section and/or percutaneous section may include tabs or similar features to facilitate manipulation and making a connection. In some embodiments, the first mating feature may include a cantilever snap-fit arm having a protrusion and the corresponding mating feature of the percutaneous end connector may define a recess configured to receive and secure the protrusion. In some embodiments, the corresponding feature of the controller end connector may include a snap-fit arm having a protrusion and the second mating feature may define a recess having a distal side that is configured to contact a proximal side of the of the protrusion. The distal side may extend inward from an outer surface of the adapter body at an angle no greater than 90°. In some embodiments, the first mating feature and the second mating feature may be positioned on different, adjacent sides of the adapter body.

In another embodiment, a driveline connector assembly for connecting a cable between an implantable blood pump and a controller is provided. The driveline connector assembly may include a percutaneous end connector configured to extend through an aperture in a patient's abdomen. The percutaneous end connector may include an internal portion configured to receive a first end of an interior driveline cable. A second end of the interior driveline cable may be configured to be coupled with the implantable blood pump. The percutaneous end connector may also include an external portion configured to extend out of the aperture in the patient's abdomen. The external portion may define a first mating feature. The driveline connector assembly may also include a controller end connector. The controller end connector may include a controller portion configured to receive a first end of an exterior driveline cable. A second end of the exterior driveline cable may be configured to be coupled with the controller. The controller end connector may also include a first engagement mechanism. The driveline connector assembly may further include a patient adapter configured to couple the percutaneous end connector with the controller end connector. The patient adapter may include a percutaneous section configured to receive the external portion of the percutaneous end connector. The percutaneous section may define a second mating feature configured to engage with the first mating feature of the external portion of the percutaneous end connector so as to secure the percutaneous end connector within the patient adapter. The patient adapter may also include a controller section configured to receive the adapter portion of the controller end connector. The controller section may define a second engagement mechanism configured to interface with the first engagement mechanism so as to releasably secure the adapter end of the controller end connector within the patient adapter.

In some embodiments, the driveline connector assembly may also include a sleeve configured to be slidably positioned around at least a portion of the first engagement mechanism, thereby preventing the first engagement mechanism from being disengaged from the second engagement feature. In some embodiments, the percutaneous end connector may include a second mating feature configured to engage with a corresponding feature of a tunneling mechanism that is configured to tunnel through a wall of the patient's abdomen. The tunneling mechanism may include a face seal configured to interface with and seal a proximal end of the percutaneous end connector. The inclusion of such a face seal may help prevent saline, blood, and/or other contaminants from reaching an electric coupling of the percutaneous end connector during the tunneling procedure. In some embodiments, the portion of the central lumen that is positioned within the percutaneous section may have a diameter of less than about 0.5 inches and the controller section may have a thickness of at least about 0.75 inches. In some embodiments, the percutaneous end connector may have a maximum diameter of no more than 0.5 inches. In some embodiments, the percutaneous end connector may further include an interface seal configured to seal an interface between the percutaneous end connector and the controller end connector when coupled within the central lumen. In some embodiments, the second engagement mechanism may define a recess having a distal side that extends inward from an outer surface of the patient adapter at an angle no greater than 90°. The first engagement mechanism may include a spring-biased arm having a protrusion configured to contact the distal side of the of the recess. In some embodiments, a maximum width of the patient adapter and the controller end connector is at least about 0.75 inches. A shape of a portion of the controller portion may match a shape of the controller end connector. The external portion of the percutaneous end connector may include a first electronic coupling and the controller end connector may include an adapter portion defining a second electronic coupling that is configured to interface with the first electronic coupling of the second side of the interior driveline cable connector. In some embodiments, the percutaneous section may have a greater thickness than the controller section, thereby increasing a form factor from the percutaneous end connector to the controller end connector.

In another embodiment, a method of connecting a driveline line cable between an implantable blood pump and an external controller is provided The method may include coupling a percutaneous portion of the driveline cable with the implantable blood pump. The percutaneous portion may terminate in a percutaneous end connector. The method may also include coupling the percutaneous end connector with a tunneling element and pulling the tunneling element through an abdominal skin wall. The method may further include coupling the percutaneous end connector with a percutaneous section at a proximal end of a patient adapter. The patient adapter may include a controller section at a distal end of the patient adapter. The controller section may have a greater form factor than the percutaneous section.

In some embodiments, coupling the percutaneous end connector with the tunneling element may include interfacing an electric coupling of the percutaneous end connector with a face seal of the tunneling element, thereby sealing the electric coupling from any substances during the formation of the hole. In some embodiments, the method may include coupling a controller end connector with the controller section of the patient adapter.

BRIEF DESCRIPTION OF THE DRAWINGS

FIG. 3 is an illustration of a blood pump in an operational position implanted in a patient's body.

FIG. 4 is a cross-sectional view of the blood pump of FIG. 3.

FIG. 6B is an end perspective view of the percutaneous end connector of FIG. 6A.

DETAILED DESCRIPTION OF THE INVENTION

Figure 1:
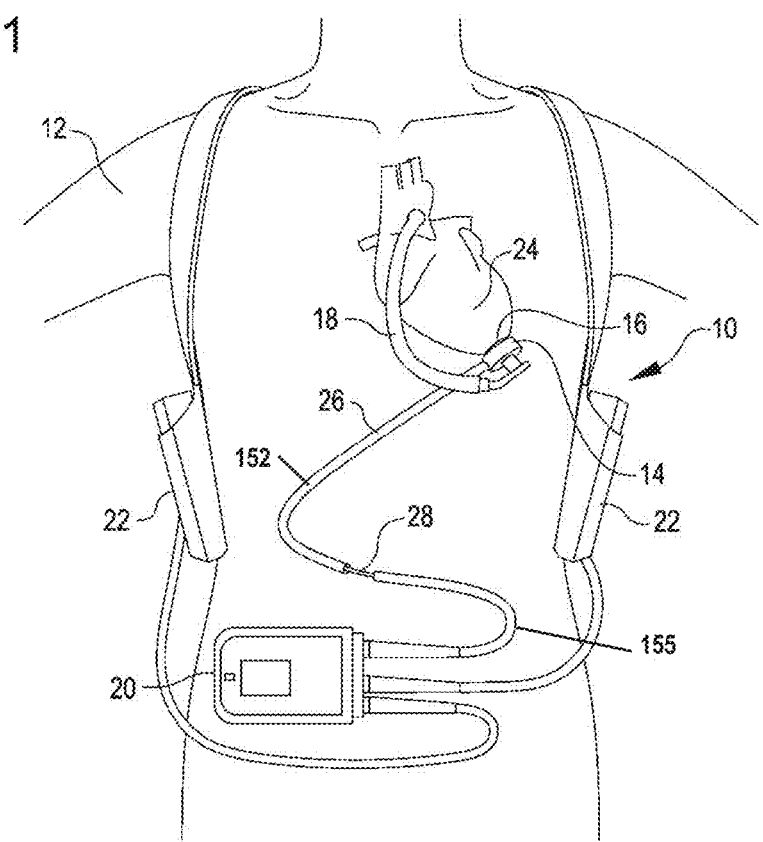
FIG. 1 is an illustration of a mechanical circulatory support system implanted in a patient's body.
Figure 2:
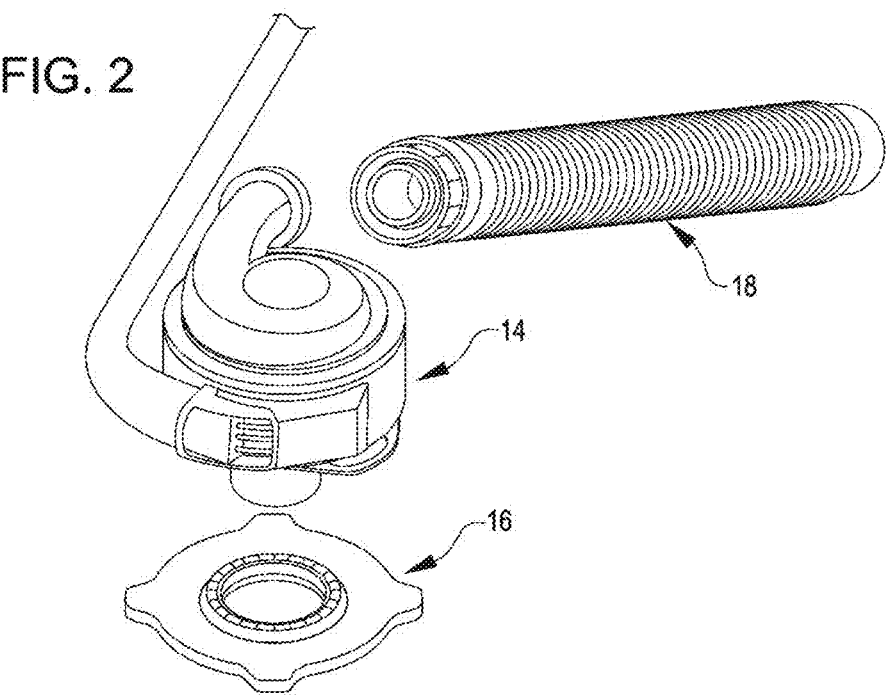
FIG. 2 is an exploded view of certain components of the circulatory support system that are implanted in a patient's body.

FIG. 1 is an illustration of a mechanical circulatory support system 10 implanted in a patient's body 12. The mechanical circulatory support system 10 comprises a implantable blood pump 14, ventricular cuff 16, outflow cannula 18, system controller 20, and power sources 22. The implantable blood pump 14 may comprise a VAD that is attached to an apex of the left ventricle, as illustrated, or the right ventricle, or both ventricles of the heart 24. The VAD may comprise a centrifugal (as shown) or axial flow pump as described in further detail herein for supporting the left ventricle (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. With reference to FIGS. 1 and 2, the blood pump 14 may be attached to the heart 24 via the ventricular cuff 16 which is sewn to the heart 24 and coupled to the blood pump 14. The other end of the blood pump 14 connects to the ascending aorta via the outflow cannula 18 so that the VAD effectively takes blood from the weakened ventricle and directs it to the ascending aorta for circulation to the rest of the patient's vascular system.

FIG. 1 is an illustration of a mechanical circulatory support system 10 during battery 22 powered operation. A driveline connects the implanted blood pump 14 to the system controller 20, which monitors system 10 operation. The driveline includes a percutaneous portion 26 that exits the patient through an abdominal aperture 29 and terminates at in-line connector 28 that connects the percutaneous portion 26 with the modular external cable 27, the other end of the modular cable being protected within the system controller, item 20 in FIG. 1. Prior to that connection of the percutaneous cable 26 and the modular cable 27 being made in the operating room, a cap or cover may be installed over the free end of the modular cable 27. An example of such a driveline having an in-line connector with which the cap may be used is described in detail in U.S. application Ser. No. 13/314,806, the contents of which are incorporated herein in their entirety for all purposes. Related controller systems applicable to the present invention are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety. The system may be powered by either one, two, or more batteries 22. It will be appreciated that although the system controller 20 and power source 22 are illustrated outside/external to the patient body, the driveline 26, system controller 20 and/or power source 22 may be partially or fully implantable within the patient, as separate components or integrated with the blood bump 14. Examples of such modifications are further described in U.S. Pat. No. 8,562,508 and U.S. Patent Publication No. 2013/0127253, all of which are incorporated herein by reference for all purposes in their entirety.

Figure 5:
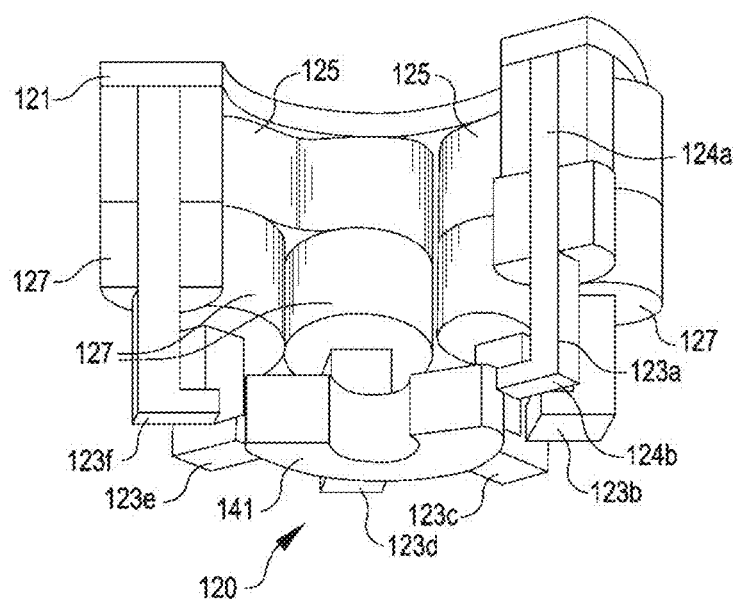
FIG. 5 is a partial cut-away perspective view of a stator of a blood pump

With reference to FIGS. 3 to 5, an example of a left ventricular assist blood pump 100 having a circular shaped housing 110 is implanted in a patient's body with a first face 111 of the housing 110 positioned against the patient's heart H and a second face 113 of the housing 110 facing away from the heart H. The first face 111 of the housing 110 includes an inlet cannula 112 extending into the left ventricle LV of the heart H. The second face 113 of the housing 110 has a chamfered edge 114 to avoid irritating other tissue that may come into contact with the blood pump 100, such as the patient's diaphragm. To construct the illustrated shape of the puck-shaped housing 110 in a compact form, a stator 120 and electronics 130 of the pump 100 are positioned on the inflow side of the housing toward first face 111, and a rotor 140 of the pump 100 is positioned along the second face 113. This positioning of the stator 120, electronics 130, and rotor 140 permits the edge 114 to be chamfered along the contour of the rotor 140, as illustrated in at least FIGS. 2-4, for example.

Referring to FIG. 4, the blood pump 100 includes a dividing wall 115 within the housing 110 defining a blood flow conduit 103. The blood flow conduit 103 extends from an inlet opening 101 of the inlet cannula 112 through the stator 120 to an outlet opening 105 defined by the housing 110. The rotor 140 is positioned within the blood flow conduit 103. The stator 120 is disposed circumferentially about a first portion 140a of the rotor 140, for example about a permanent magnet 141. The stator 120 is also positioned relative to the rotor 140 such that, in use, blood flows within the blood flow conduit 103 through the stator 120 before reaching the rotor 140. The permanent magnet 141 has a permanent magnetic north pole N and a permanent magnetic south pole S for combined active and passive magnetic levitation of the rotor 140 and for rotation of the rotor 140. The rotor 140 also has a second portion 140b that includes impeller blades 143. The impeller blades 143 are located within a volute 107 of the blood flow conduit such that the impeller blades 143 are located proximate to the second face 113 of the housing 110.

The puck-shaped housing 110 further includes a peripheral wall 116 that extends between the first face 111 and a removable cap 118. As illustrated, the peripheral wall 116 is formed as a hollow circular cylinder having a width W between opposing portions of the peripheral wall 116. The housing 110 also has a thickness T between the first face 111 and the second face 113 that is less than the width W. The thickness T is from about 0.5 inches to about 1.5 inches, and the width W is from about 1 inch to about 4 inches. For example, the width W can be approximately 2 inches, and the thickness T can be approximately 1 inch.

The peripheral wall 116 encloses an internal compartment 117 that surrounds the dividing wall 115 and the blood flow conduit 103, with the stator 120 and the electronics 130 disposed in the internal compartment 117 about the dividing wall 115. The removable cap 118 includes the second face 113, the chamfered edge 114, and defines the outlet opening 105. The cap 118 can be threadedly engaged with the peripheral wall 116 to seal the cap 118 in engagement with the peripheral wall 116. The cap 118 includes an inner surface 118a of the cap 118 that defines the volute 107 that is in fluid communication with the outlet opening 105.

Within the internal compartment 117, the electronics 130 are positioned adjacent to the first face 111 and the stator 120 is positioned adjacent to the electronics 130 on an opposite side of the electronics 130 from the first face 111. The electronics 130 include circuit boards 131 and various components carried on the circuit boards 131 to control the operation of the pump 100 (e.g., magnetic levitation and/or drive of the rotor) by controlling the electrical supply to the stator 120. The housing 110 is configured to receive the circuit boards 131 within the internal compartment 117 generally parallel to the first face 111 for efficient use of the space within the internal compartment 117. The circuit boards also extend radially-inward towards the dividing wall 115 and radially-outward towards the peripheral wall 116. For example, the internal compartment 117 is generally sized no larger than necessary to accommodate the circuit boards 131, and space for heat dissipation, material expansion, potting materials, and/or other elements used in installing the circuit boards 131. Thus, the external shape of the housing 110 proximate the first face 111 generally fits the shape of the circuits boards 131 closely to provide external dimensions that are not much greater than the dimensions of the circuit boards 131.

With continued reference to FIGS. 4 and 5, the stator 120 includes a back iron 121 and pole pieces 123a-123f arranged at intervals around the dividing wall 115. The back iron 121 extends around the dividing wall 115 and is formed as a generally flat disc of a ferromagnetic material, such as steel, in order to conduct magnetic flux. The back iron 121 is arranged beside the control electronics 130 and provides a base for the pole pieces 123a-123f.

Each of the pole piece 123a-123f is L-shaped and has a drive coil 125 for generating an electromagnetic field to rotate the rotor 140. For example, the pole piece 123a has a first leg 124a that contacts the back iron 121 and extends from the back iron 121 towards the second face 113. The pole piece 123a may also have a second leg 124b that extends from the first leg 124a through an opening of a circuit board 131 towards the dividing wall 115 proximate the location of the permanent magnet 141 of the rotor 140. In an aspect, each of the second legs 124b of the pole pieces 123a-123f is sticking through an opening of the circuit board 131. In an aspect, each of the first legs 124a of the pole pieces 123a-123f is sticking through an opening of the circuit board 131. In an aspect, the openings of the circuit board are enclosing the first legs 124a of the pole pieces 123a-123f.

In a general aspect, the implantable blood pump 100 may include a Hall sensor that may provide an output voltage, which is directly proportional to a strength of a magnetic field that is located in between at least one of the pole pieces 123a-123f and the permanent magnet 141, and the output voltage may provide feedback to the control electronics 130 of the pump 100 to determine if the rotor 140 and/or the permanent magnet 141 is not at its intended position for the operation of the pump 100. For example, a position of the rotor 140 and/or the permanent magnet 141 may be adjusted, e.g., the rotor 140 or the permanent magnet 141 may be pushed or pulled towards a center of the blood flow conduit 103 or towards a center of the stator 120.

Each of the pole pieces 123a-123f also has a levitation coil 127 for generating an electromagnetic field to control the radial position of the rotor 140. Each of the drive coils 125 and the levitation coils 127 includes multiple windings of a conductor around the pole pieces 123a-123f. Particularly, each of the drive coils 125 is wound around two adjacent ones of the pole pieces 123, such as pole pieces 123d and 123e, and each levitation coil 127 is wound around a single pole piece. The drive coils 125 and the levitation coils 127 are wound around the first legs of the pole pieces 123, and magnetic flux generated by passing electrical current though the coils 125 and 127 during use is conducted through the first legs and the second legs of the pole pieces 123 and the back iron 121. The drive coils 125 and the levitation coils 127 of the stator 120 are arranged in opposing pairs and are controlled to drive the rotor and to radially levitate the rotor 140 by generating electromagnetic fields that interact with the permanent magnetic poles S and N of the permanent magnet 141. Because the stator 120 includes both the drive coils 125 and the levitation coils 127, only a single stator is needed to levitate the rotor 140 using only passive and active magnetic forces. The permanent magnet 141 in this configuration has only one magnetic moment and is formed from a monolithic permanent magnetic body 141. For example, the stator 120 can be controlled as discussed in U.S. Pat. No. 6,351,048, the entire contents of which are incorporated herein by reference for all purposes. The control electronics 130 and the stator 120 receive electrical power from a remote power supply via a cable 119 (FIG. 3). Further related patents, namely U.S. Pat. Nos. 5,708,346, 6,053,705, 6,100,618, 6,222,290, 6,249,067, 6,278,251, 6,351,048, 6,355,998, 6,634,224, 6,879,074, and 7,112,903, all of which are incorporated herein by reference for all purposes in their entirety.

The rotor 140 is arranged within the housing 110 such that its permanent magnet 141 is located upstream of impeller blades in a location closer to the inlet opening 101. The permanent magnet 141 is received within the blood flow conduit 103 proximate the second legs 124b of the pole pieces 123 to provide the passive axial centering force though interaction of the permanent magnet 141 and ferromagnetic material of the pole pieces 123. The permanent magnet 141 of the rotor 140 and the dividing wall 115 form a gap 108 between the permanent magnet 141 and the dividing wall 115 when the rotor 140 is centered within the dividing wall 115. The north permanent magnetic pole N and the south permanent magnetic pole S of the permanent magnet 141 provide a permanent magnetic attractive force between the rotor 140 and the stator 120 that acts as a passive axial centering force that tends to maintain the rotor 140 generally centered within the stator 120 and tends to resist the rotor 140 from moving towards the first face 111 or towards the second face 113. When the gap 108 is smaller, the magnetic attractive force between the permanent magnet 141 and the stator 120 is greater, and the gap 108 is sized to allow the permanent magnet 141 to provide the passive magnetic axial centering force having a magnitude that is adequate to limit the rotor 140 from contacting the dividing wall 115 or the inner surface 118a of the cap 118. The rotor 140 also includes a shroud 145 that covers the ends of the impeller blades 143 facing the second face 113 that assists in directing blood flow into the volute 107. The shroud 145 and the inner surface 118a of the cap 118 form a gap 109 between the shroud 145 and the inner surface 118a when the rotor 140 is levitated by the stator 120.

As blood flows through the blood flow conduit 103, blood flows through a central aperture 141a formed through the permanent magnet 141. Blood also flows through the gap 108 between the rotor 140 and the dividing wall 115 and through the gap 109 between the shroud 145 and the inner surface 108a of the cap 118.

Because the rotor 140 in the example pump 100 is radially suspended by active control of the levitation coils 127 as discussed above, and because the rotor 140 is axially suspended by passive interaction of the permanent magnet 141 and the stator 120, no rotor levitation components are needed proximate the second face 113. The incorporation of all the components for rotor levitation in the stator 120 (i.e., the levitation coils 127 and the pole pieces 123) allows the cap 118 to be contoured to the shape of the impeller blades 143 and the volute 107. Additionally, incorporation of all the rotor levitation components in the stator 120 eliminates the need for electrical connectors extending from the compartment 117 to the cap 118, which allows the cap to be easily installed and/or removed and eliminates potential sources of pump failure.

In use, the drive coils 125 of the stator 120 generates electromagnetic fields through the pole pieces 123 that selectively attract and repel the magnetic north pole N and the magnetic south pole S of the rotor 140 to cause the rotor 140 to rotate within stator 120. For example, the Hall sensor may sense a current position of the rotor 140 and/or the permanent magnet 141, wherein the output voltage of the Hall sensor may be used to selectively attract and repel the magnetic north pole N and the magnetic south pole S of the rotor 140 to cause the rotor 140 to rotate within stator 120. As the rotor 140 rotates, the impeller blades 143 force blood into the volute 107 such that blood is forced out of the outlet opening 105. Additionally, the rotor draws blood into pump 100 through the inlet opening 101. As blood is drawn into the blood pump by rotation of the impeller blades 143 of the rotor 140, the blood flows through the inlet opening 101 and flows through the control electronics 130 and the stator 120 toward the rotor 140. Blood flows through the aperture 141a of the permanent magnet 141 and between the impeller blades 143, the shroud 145, and the permanent magnet 141, and into the volute 107. Blood also flows around the rotor 140, through the gap 108 and through the gap 109 between the shroud 145 and the inner surface 118a of the cap 118. The blood exits the volute 107 through the outlet opening 105, which may be coupled to an outflow cannula.

The connection between the components within the body and those outside of the body presents many challenges. Oftentimes, patients requiring the assistance of a VAD are elderly, and in many cases suffer from one more of arthritis, vision loss, cognitive issues, and the like. Given these circumstances, it is desirable to have a driveline connection, such as in-line connector 28, that is large and easy to manipulate for those who lack dexterity and/or vision. However, it is also important to keep the aperture in the patient's abdomen and tunneled passageway through the tissue as small as possible to promote rapid healing, prevent infection, reduce bleeding, and for other health and safety reasons. These two size requirements run counter to one another. Moreover, conventional left ventricular assist systems (LVAS) utilize a single driveline of uniform size and shape extending from the pump to the controller. Due to the above-mentioned complications associated with the implanted portion of the driveline, such conventional drivelines are sized as small as possible. To address these and other issues, the exemplary LVAS described herein utilizes two driveline assembly connectors having differing sizes, a smaller percutaneous end connector and a larger controller end connector, may be coupled to one another using a patient adapter.

The patient adapter of the present invention increases a form factor of the connection between a percutaneous side to a patient controller side of the system. This allows a small percutaneous portion of the driveline cable assembly to be coupled with a left ventricle assist device and bored through the patient's abdominal wall. This enables the resultant hole in the patient's abdomen to be quite small, while providing a larger connection component that is easy to grasp and manipulate for most patients. The controller end connector may then be coupled to the larger end of the patient adapter without the use of any tools to complete a circuit between the controller and the left ventricle assist device. Such an assembly limits the number of connections that need to be made by a patient to a single connection, while still satisfying both size requirements of left ventricle assist device systems.

Figure 6A:
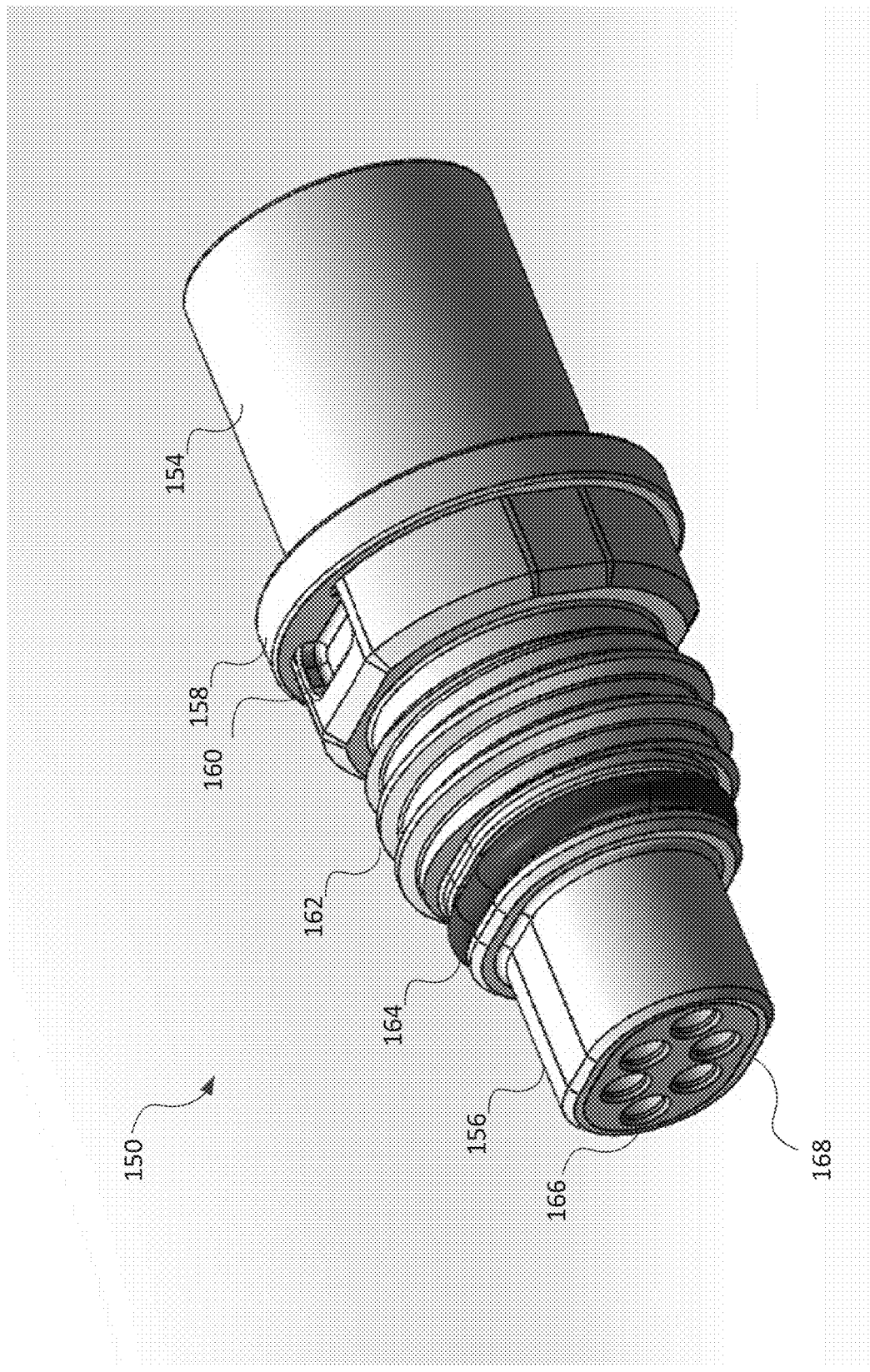
FIG. 6A is an isometric view of a percutaneous end connector of a driveline cable assembly.

FIG. 6A depicts one embodiment of a percutaneous end connector 150 that is coupled with the percutaneous portion 26 of driveline cable 152. The percutaneous portion 26 extends internally within the patient's chest where it is coupled with the left ventricle assist device 14. The percutaneous end connector 150 is configured to be tunneled through the wall of the patient's abdomen. As such, it is desirable for the percutaneous connector end 150 to be as small as possible to help prevent infection and to as to promote quicker healing. The percutaneous end connector 150 preferably has a maximum diameter of less than about 0.50 inches, and more preferably less than about 0.40 inches. The percutaneous end connector 150 is positioned by the surgeon so that a portion of the percutaneous end connector 150 is contained within an internal cavity formed in the chest. The percutaneous end connector 150 may include an internal portion 154 configured to receive one end of the interior or percutaneous portion 26 of driveline cable 152, with the other end of the percutaneous portion 26 being coupled with the blood pump 14. The internal portion 154 of the percutaneous end connector 150 may be positioned within the internal cavity or incision made in the abdomen. The percutaneous end connector 150 may also include an external portion 156 configured to extend out of the internal cavity of the patient's abdomen. In some embodiments, the internal portion 154 and the external portion 156 may be separated by a shoulder or flange 158 formed in a medial portion of the percutaneous end connector 150. Typically, the flange 158 has the maximum diameter of the percutaneous end connector 150, with the interior portion 154 and the external portion 156 being somewhat thinner.

Figure 8A:
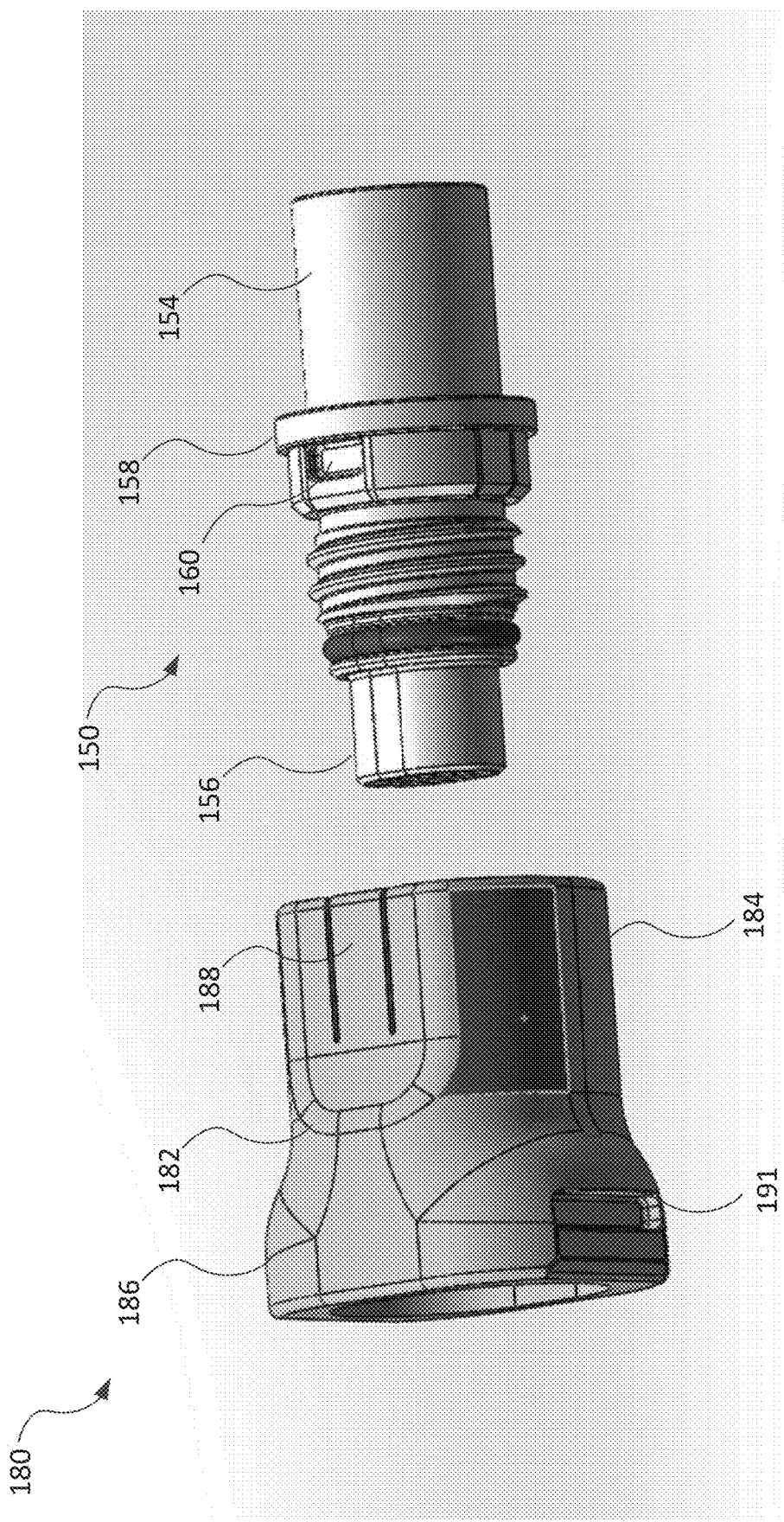
FIG. 8A is an isometric view of a percutaneous end connector and a patient adapter in a disconnected configuration.
Figure 8B:
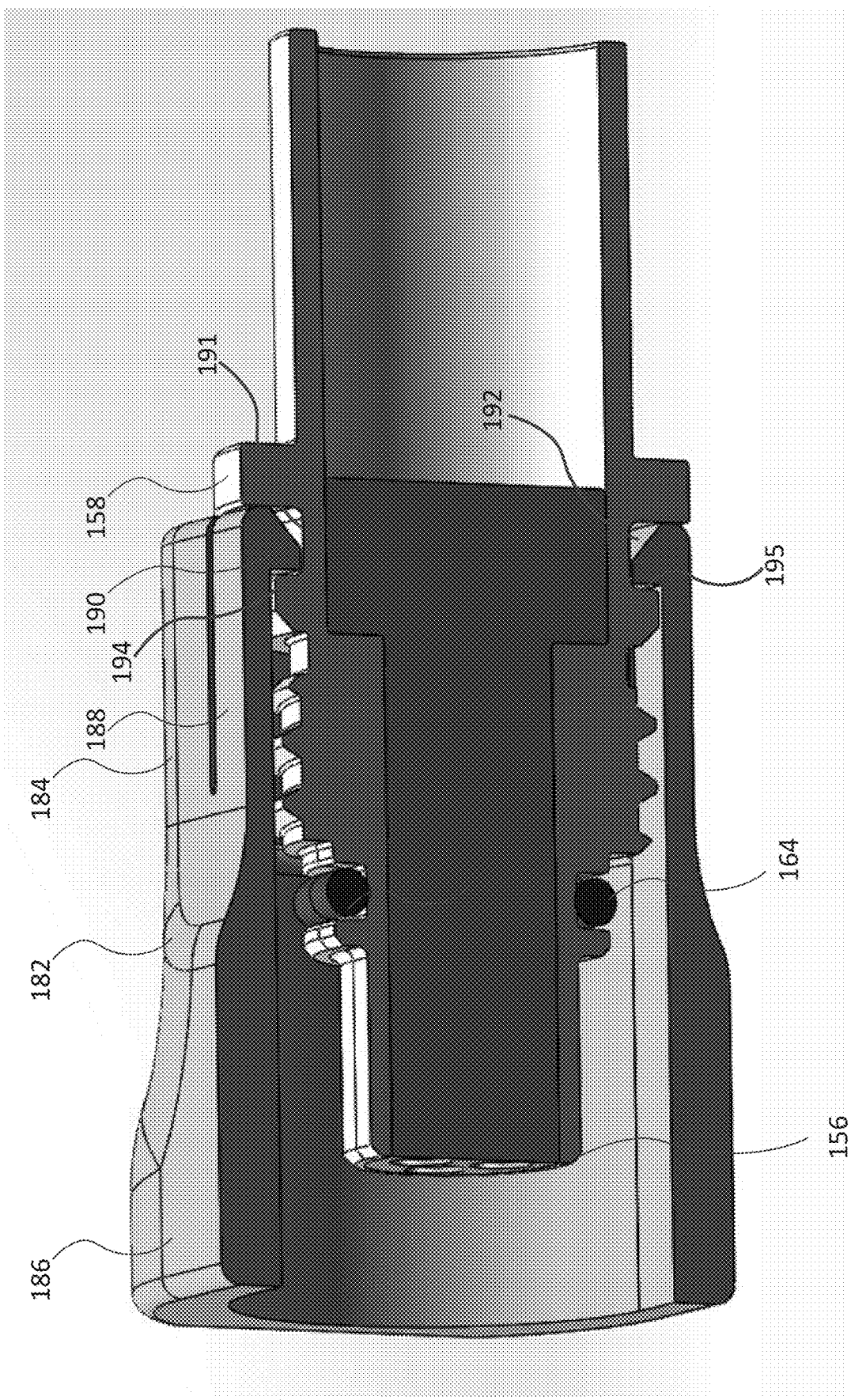
FIG. 8B is a cross-sectional view of the percutaneous end connector and the patient adapter of FIG. 8A in a connected configuration.

The external portion 156 may define a first mating feature that enables the percutaneous end connector 150 to be secured to a patient adapter 180 as shown in FIGS. 8A and 8B. For example, the first mating feature may define at least one recess 160 formed in an exterior surface of the external portion 156. In some embodiments, one or more recesses 160 may be positioned on opposite surfaces of the external portion 156. For example, a top surface and a bottom surface of the external portion 156 may each include a recess 160. The recesses 160 may each be configured to receive and secure a protrusion 190 or other mating feature of a patient adaptor 180. For example, a distal surface 192 of the protrusion 190 may be beveled. During installation of the patient adapter 180, the distal surface 192 may contact an exterior surface of the external portion 156 of the percutaneous end connector 150, which may cause a cantilever snap-fit arm 188 to deflect outward until the protrusion 190 is aligned with the recess 160. The protrusion 190 may then snap into the recess 160, causing a proximal surface of the protrusion 190 to slide against a proximal side wall of the recess 160. Oftentimes, the proximal side wall may extend from an outer surface of the external portion 156 of the percutaneous end connector 150 at an angle of no less than 90°. Such design helps ensure that the protrusion 190 stays engaged within the recess 160 at all times, including when subjected to pulling forces along the longitudinal axis of the patient adapter 180.

Figure 7A:
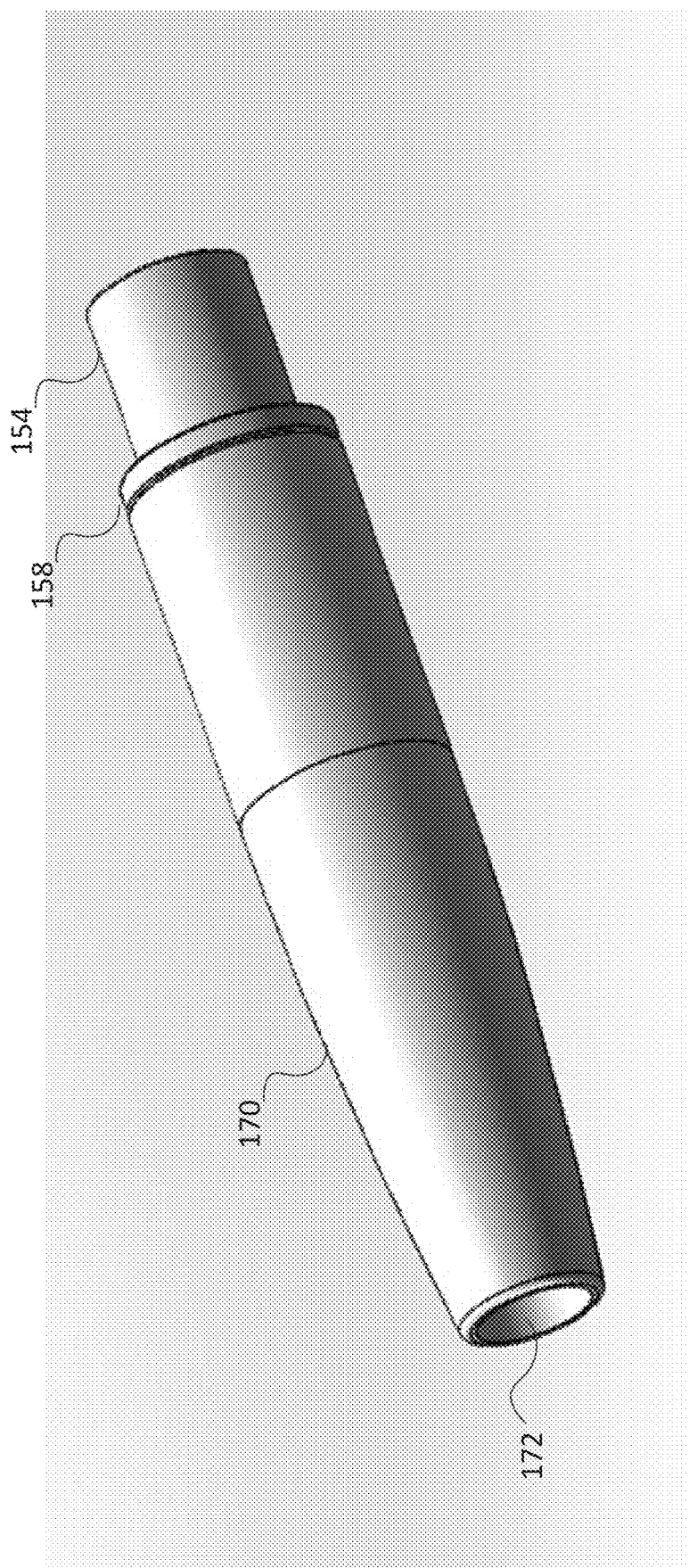
FIG. 7A is an isometric view of a tunneling element and percutaneous end connector.
Figure 7B:
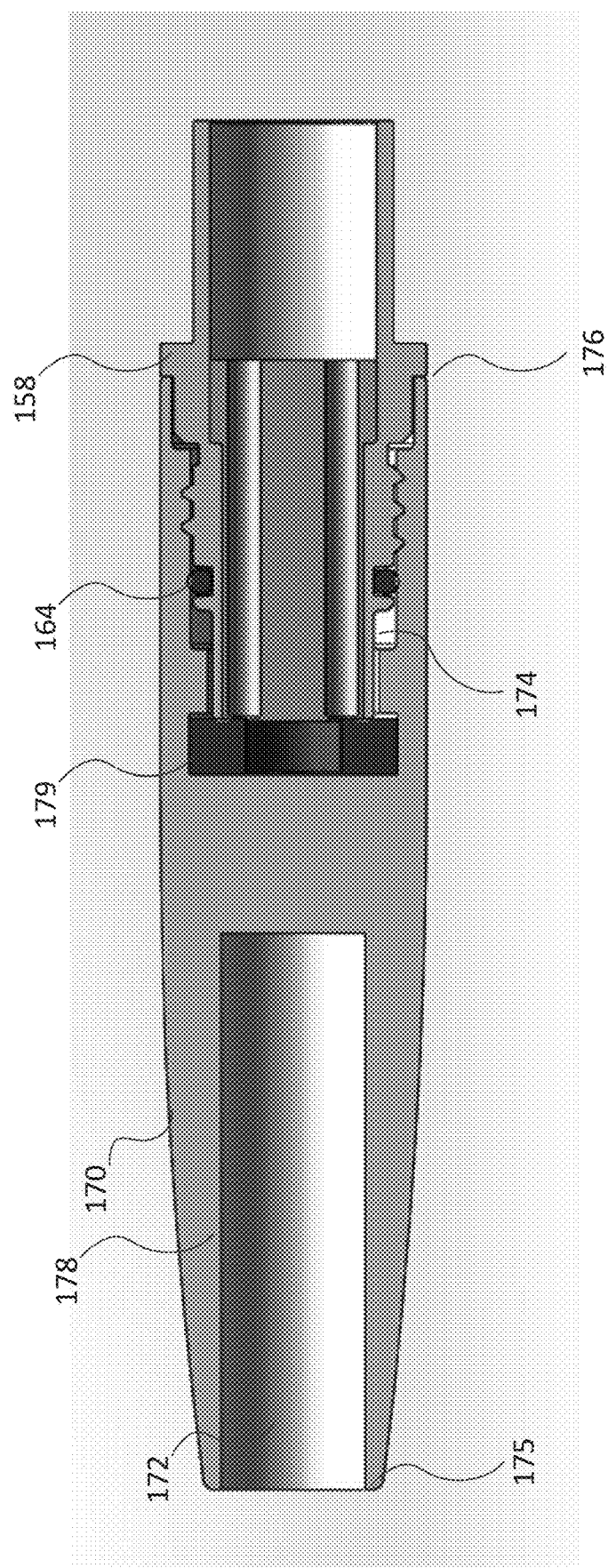
FIG. 7B is a cross-sectional view of the tunneling element and percutaneous end connector of FIG. 7A.

The external portion 156 may also include a second mating feature that is configured to engage with a corresponding feature of a tunneling element 170 as shown in FIGS. 7A and 7B. For example, the second mating feature may include a threaded portion 162 that allows the tunneling element 170 to be secured to the percutaneous end connector 150. While shown here as separate features, in some embodiments the first mating feature and the second mating feature may be a single feature that may be used to couple the percutaneous end connector 150 to the tunneling element 170 during placement/installation of the driveline cable 152, and may later be used to couple the percutaneous end connector 150 with the patient adapter 180. In some embodiments, the external portion 156 may include a sealing element 164 that may help seal an interface formed between surfaces of the tunneling element 170 and the percutaneous end connector 150 during the implantation of the percutaneous end connector 150 and between the percutaneous end connector 150 and the controller end connector 196 in a final configuration.

As best shown in FIG. 6B, the external portion 156 may also include an electric coupling 166 that allows the percutaneous portion 26 of the driveline cable 152 to be electrically coupled with an external portion 155 of the driveline cable 152. In some embodiments, any electrical connections described herein may be insulated using polyether ether ketone (PEEK). The electric coupling 166 may include a number of pins and/or a number of receptacles to receive pins. In some embodiments, the pins and/or receptacles of the electric coupling 166 may be arranged in a symmetric pattern, thereby allowing a user to connect the electric coupling 166 to a corresponding electric coupling 204 on the controller end connector 196 in multiple orientations. As just one example, the electric coupling 166 may include a number of receptacles (shown here with six receptacles, although other numbers may be used based on the particular data and power needs of the left ventricle assist system) that are symmetrically arranged such that an electric coupling 204 of the controller end connector 196 may be connected in at least two different orientations, such as at 90°, 180°, or other regular intervals. In some embodiments, the percutaneous end connector 150 may have a generally circular outer periphery, which allows a symmetrical tunneling element 170 to be used to bore the internal cavity in the patient's abdomen. While shown here having a distal end 168 of the external portion 156 (which is proximate the electric coupling 166) that has a non-circular outer periphery, it will be appreciated that other shapes may be used. For example, the distal end 168 may have a generally stadium-shaped periphery, having a rectangle with top and bottom lengths with ends that are capped off with semicircles, however other non-circular shapes may also be contemplated. The use of such a shaped distal end 168 along with a symmetrical electric coupling 166 makes it easier for a patient to align the electric coupling 166 with the electric coupling 204 of the controller end connector 196, as the alignment of the non-circular shapes will result in the alignment of the electric couplings 166 and 204 with one another.

FIG. 7A depicts the percutaneous end connector 150 coupled with tunneling element 170. Such a coupling may be done by surgical staff during the implantation process of the left ventricle assist system. Tunneling element 170 may have a tapered profile such that the tunneling element 170 is generally bullet-shaped. The tunneling element 170 may also define a central opening 172 that may extend from a front edge 175 of the tunneling element 170 through at least a portion of a length of the tunneling element 170. The central opening 172 may be configured to receive a distal end of a lance or other puncturing object (not shown). The lance may be secured within the central opening 172 using a fastening mechanism. For example, walls of the central opening 172 may be threaded such that a lance having corresponding threads may be screwed into the central opening 172 to secure the lance within the central opening 172. It will be appreciated that in some embodiments, other fastening techniques, such as snap-fits connectors, press-fit connections, magnets, and the like may be used to couple a lance within the central opening 172.

As shown in FIG. 7B, the tunneling element 170 may define a second central opening 174 formed from a rear surface 176 of the tunneling element 170. The second central opening 174 may be configured to receive the external portion 156 of the percutaneous end connector 150. An interior surface 178 of the second central opening 174 may include a feature that is configured to engage with the second mating feature of the external portion 156 of the percutaneous end connector 150. For example, the interior surface 178 may be threaded to enable the threaded portion 162 of the percutaneous end connector 150 to be screwed into the second central opening 174 for securement within. While described here using a threaded engagement between the second central opening 174 and the percutaneous end connector 150, it will be appreciated that other fastening mechanisms that are capable of handling the high forces present during the tunneling process may also be used. In some embodiments, the tunneling element 170 may be secured to the percutaneous end connector 150 using the same mating feature as used to couple the percutaneous end connector 150 with a patient adaptor 180. In such embodiments, the type of fastener may be chosen based on the needs to be strong enough to withstand the tunneling process and the need to be permanent or semi-permanent. For example, while threaded fasteners may provide the necessary strength for tunneling, the threaded fasteners may be too easily loosened and removed to provide the necessary permanence as needed by the patient adapter connection. As these connections are made by surgical staff, such connections may require the use of tools for attachment or disengagement with the tunneling element 170 and/or the patient adapter 180. While described here as having two central openings, it will be appreciated that a tunneling element 170 may have a single central opening that extends entirely through a length of the tunneling element 170.

In some embodiments, the rear surface 176 of the tunneling element 170 may be positioned against, or proximate to, the flange 158 of the percutaneous end connector 150. When the rear surface 176 is positioned against the flange 158, an interior of the connection between the tunneling element 170 and the percutaneous end connector is largely sealed from any contaminants that could possibly be introduced to the electric coupling 166 of the percutaneous end connector 150. To further help seal the electric coupling 166, a face seal 179 may be provided within the second central opening 172. The face seal 179 may be formed of silicon, rubber, and/or another waterproof material. Oftentimes, the face seal 179 is in the form of a disk that is configured to cover an entire face of the electric coupling 166, although in other embodiments the face seal 179 may be a ring that prevents water and other contaminants from getting past the ring to the electric coupling 166. In some embodiments, the face seal 179 may be a disk having edges that extend beyond an outer periphery of the face of the electric coupling 166. As the external portion 156 of the percutaneous end connector 150 is inserted to its final depth within the second central opening 174 (which may be set using the flange 158), the face of the electric coupling 166 presses against the face seal 179, thereby compressing the face seal and forming a watertight seal around the face of the electric coupling 166. Sealing element 164 may also provide a seal between the interior surface 178 and an exterior surface of the external portion 156. The use of multiple seals helps ensure that contaminants do not reach the electric coupling 166 during the tunneling process. Upon creation of the internal cavity in the patient's abdomen, the internal portion 154 of the percutaneous portion 26 of the driveline cable 152 will be disposed within the internal cavity, while the external portion 156 of the driveline cable 152 and percutaneous end connector 150 extend outside of the patient's abdomen.

Once the percutaneous end connector 150 has been tunneled out of the patient's abdomen, a driveline connector adapter or patient adapter 180 may be installed. As the percutaneous end connector 150 has a fairly small profile (having a diameter of no more than about 0.5 inches), the patient adapter 180 is designed to be coupled with the percutaneous end connector 150 by a member of the surgical staff. The patient adapter 180 increases a form factor of the small percutaneous end connector 150 to provide a component that is easier to grip and manipulate for older and/or less dexterous patients to handle. For example, the form factor may be defined by the outer periphery of the various sections of the patient adapter. At least one major dimension (width and/or height) of the outer periphery may have a minimum thickness that is sufficiently large so as to be easily grasped and manipulated by patients who lack dexterity and/or clear vision. As shown in FIG. 8A, the patient adapter 180 may include an adapter body 182. The adapter body 182 may have a percutaneous section 184 that is positioned at one end of the adapter body 182 and a controller section 186 that is positioned at the opposite end of the adapter body 182. In some embodiments, the percutaneous section 184 may include a mating feature that is configured to engage a corresponding mating feature of the percutaneous end connector 150 so as to secure the percutaneous end connector 150 with the patient adapter 180. For example, each mating feature of the percutaneous section 184 may include at least one cantilevered snap-fit arm 188 that includes a protrusion 190. In some embodiments, a snap-fit arm 188 or other mating feature may be provided on opposite surfaces of the percutaneous section 184. For example, a top surface and a bottom surface of the percutaneous section 184 may each include at least one cantilevered snap-fit arm 188. The protrusion 190 may be configured to be inserted within the recess 160 of the percutaneous end connector 150 as shown in FIG. 8B. A distal surface 192 of the protrusion 190 may be beveled such that during installation of the patient adapter 180, the distal surface 192 may contact an exterior surface of the external portion 156 of the percutaneous end connector 150, which may cause the cantilevered snap-fit arm 188 to deflect outward until the protrusion 190 is aligned with the recess 160. The protrusion 190 may then snap into the recess 160, causing a proximal surface 194 of the protrusion 190 to slide against a proximal side wall 195 of the recess 160. Oftentimes, the proximal side wall 195 may extend from an outer surface of the percutaneous end connector 150 at an angle of no less than 90°. Such design helps ensure that the protrusion 190 stays engaged within the recess 160 at all times, including when subjected to pulling forces along the longitudinal axis of the percutaneous end connector 150. To further strengthen this connection, the protrusion 190 may have a hook-like shape that engages the peripheral side wall 195, which may be at an angle less than 90° relative to the exterior surface of the percutaneous end connector 150, thereby forming a latch that is heavily resistant to lateral forces. Once the percutaneous end connector 150 is fully inserted within the patient adapter 180, a distal end of the patient adapter 180 will be positioned against the flange 158, generally sealing the interior of the connection and setting a maximum depth of insertion of the percutaneous end connector 150.

Turning back to FIG. 8A, the controller section 186 may include a second mating feature configured to releasably engage a corresponding mating or engagement feature of the controller end connector 196 so as to secure the controller end connector 196 with the patient adapter 180. This allows the controller end connector 196 to be electrically coupleable with the percutaneous end connector 150. For example, the second mating feature may include at least one recess 191 formed in an exterior surface of the controller section 186. In some embodiments, a recess 191 or other mating feature may be provided on opposite surfaces of the controller section 186. For example, a first side and a second side of the controller section 186 may each include at least one recess 191. The recesses 191 may each be configured to receive a protrusion 210 of a pivotable snap-fit arm 208 of the controller end connector 196. In some embodiments, the first mating feature and the second mating feature are positioned on different, adjacent sides of the adapter body. For example, the first mating feature may include snap-fit arms and/or other features formed on or coupled with the top and/or bottom of the adapter body 182, while the second mating feature may include recesses and/or other features formed on or coupled with a first side and/or a second side of the adapter body 182. As shown in FIG. 8B, the adapter body 182 defines a central lumen 198 that extends through an entire length of the adapter body 182 and may receive the electric coupling 166 of the percutaneous end connector 150 and an electric coupling 204 of the controller end connector 196. For example, a portion of the central lumen 198 that is positioned within the percutaneous section 184 may be configured to receive an end of the percutaneous end connector 150, while a portion of the central lumen 109 that is positioned within the controller section 186 may be configured to receive an end of the controller end connector 196.

To help patients more easily handle the patient adapter 180, the adapter body 182 may have a maximum thickness of at least 0.75 inches. In some embodiments, all or a substantial portion of the adapter body 182 may have the maximum thickness, while in other embodiments only half or a smaller portion of the adapter body 182 has the maximum thickness. For example, the percutaneous section 184 may have a smaller width than the controller section 186. The percutaneous section 184 may have a width that is only slightly greater than a diameter of the percutaneous end connector 150. This allows the cantilevered snap-fit arm 188 to be in plane with and/or protruding only slightly beyond an outer periphery of the percutaneous end connector 150. Due to the small size of both the percutaneous end connector 150 and the percutaneous section 184, these components may be coupled with one another by the surgical team. The adapter body 182 may taper or otherwise widen to its maximum thickness towards the controller section 186, thereby increasing a form factor from the first end of the adapter body to the second end of the adapter body 182.

Oftentimes, the adapter body 182 has a non-circular cross-sectional shape, and oftentimes a shape that has sides that are distinguishable using touch alone. For example, the adapter body 182 may have a cross-sectional shape of a rectangle with rounded corners. Such a cross-section allows a user to identify a proper orientation of the adapter body 182 when attempting to align and connect the adapter body 182 with the controller end connector 196. Such cross-sections also eliminate the need for different textures and/or alignment features to help patients align the components to ensure that the electric couplings 166 and 204 may be properly engaged. However, in some embodiments, such differing textures, markings, and/or other alignment aids may be included to further contribute to the ease of connection. Once coupled together by surgical staff, the percutaneous end connector 150 and the patient adapter 180 are typically not disengaged from one another, as that would require surgical staff to perform another coupling process. As such, it is important that the mating features or other securement mechanisms are designed to maintain a permanent (or semi-permanent) connection.

Figure 9:
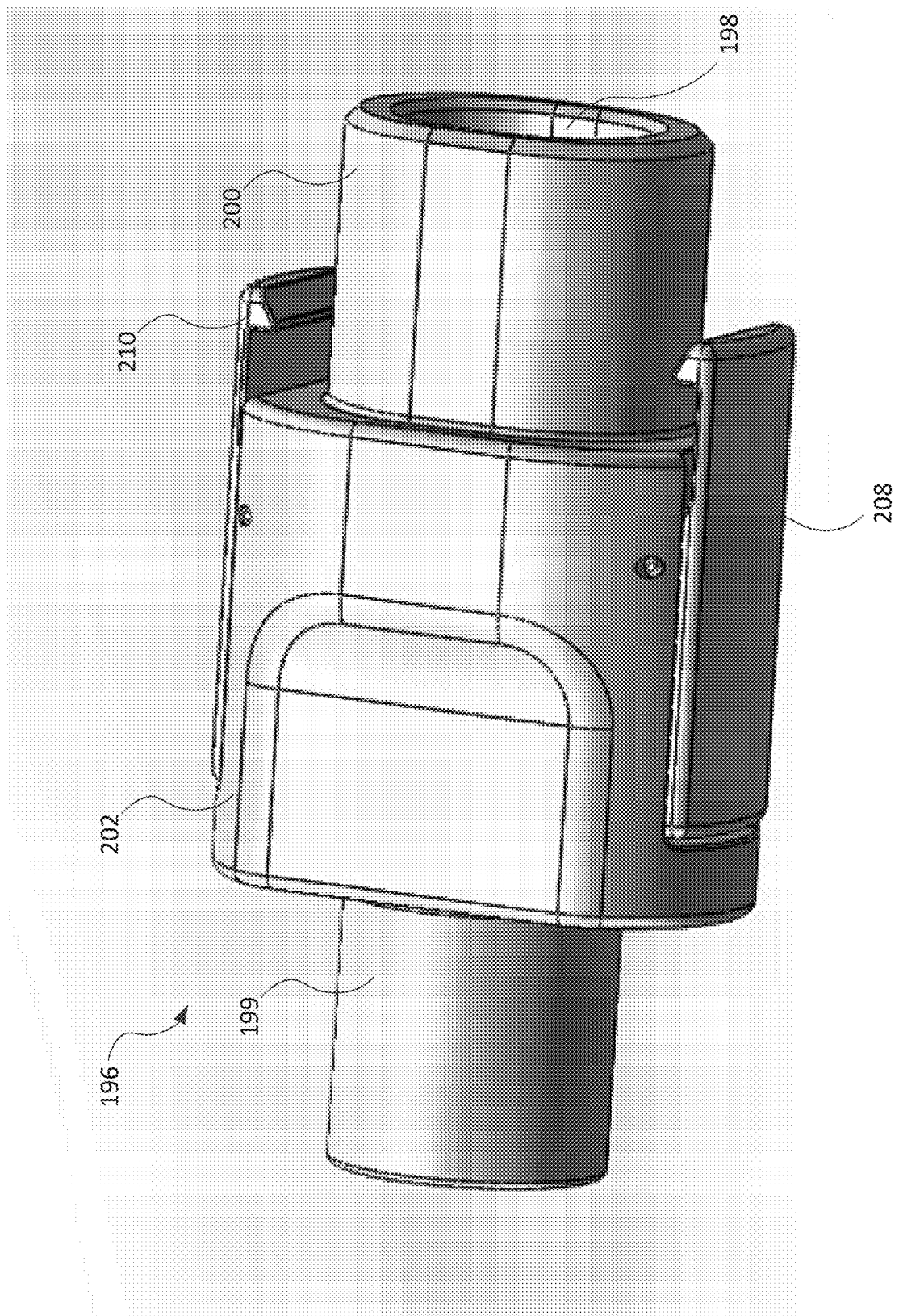
FIG. 9 is a perspective view of a controller end connector.

FIG. 9 depicts one embodiment of a controller end connector 196. Controller end connector 196 may include a controller portion 199 and an adapter portion 200 separated by a medial portion 202. The controller portion 199 may be configured to receive a first end of the external portion 155 of the driveline cable 152, with the other end of the external portion 155 of the driveline cable 152 being coupled with the controller 20. The adapter portion 200 may include an electronic coupling 204 that is configured to interface with the electric coupling 166 of the percutaneous end connector 150. For example, the electronic coupling 204 may include one or more pins (not shown) or other electric connectors that may interface with the corresponding features of the electric coupling 166. Any pins or other electronic connections may include PEEK insulation. The electric coupling 204 also include an exterior 206 that is configured to be inserted within the central lumen 198 of the patient adapter 180. The exterior 206 may be sized and shaped to fit snuggly within the central lumen 198. The adapter portion 200 may also include an engagement mechanism that may interface with the corresponding mating feature of the patient adapter 180. For example, the engagement mechanism may include at least one pivotable arm 208. In some embodiments, multiple surfaces of the adapter portion 200 may include at least one pivotable arm 208 or other mating feature. For example, a first side and a second side of the adapter portion 200 may each include at least one pivotable arm 208. Each pivotable arm 208 may extend from the medial portion 202 to a position over the exterior 206 of the electric coupling 204. A distal end 212 of the pivotable arm 208 may include a protrusion 210 that is configured to engage with the recess 191 on the controller section 186 of the patient adapter 180. To further strengthen this connection, the protrusion 210 may have a hook-like shape that engages a peripheral side wall of the recess 191, which may be at an angle less than 90° relative to the exterior surface of the controller section 186 of the patient adapter 180, thereby forming a latch that is heavily resistant to lateral forces.

Figure 10A:
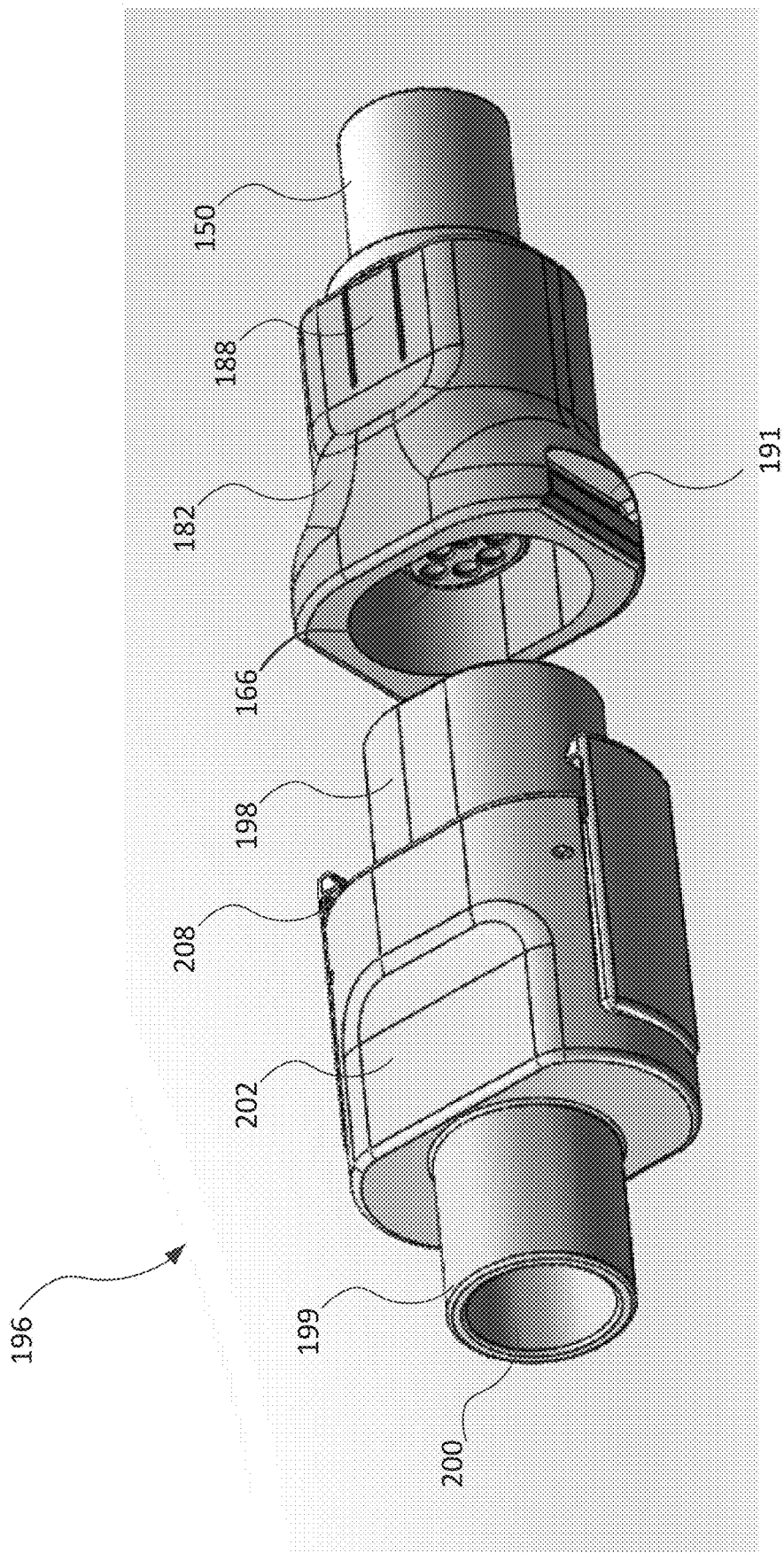
FIG. 10A is an isometric view of a driveline cable assembly in a disconnected configuration.

FIG. 10A depicts the connection a patient must make between the controller end connector 196 and the patient adapter 180. Here, the patient adapter 180 is already coupled with the percutaneous end connector 150. Such a connection is often made by the surgical staff during the implantation process. The coupling of the controller end connector 196 and the patient adapter 180 is made easier for the patient by the larger form factor provided by the greater thicknesses of both components. The alignment of the controller end connector 196 and the patient adapter 180 may be simplified by the outer peripheries of both components having substantially the same cross-sectional size and shape. Oftentimes, the outer peripheries will be shaped to have one side or pair of sides that are different than the others. For example, rectangular or stadium shapes may be used as the longer sides of each component may be aligned with one another to help align electric coupling 204 within the central lumen 198 of the patient adapter 180. For example, the adapter body 182 and/or controller end connector 196 may have widths that are greater than their heights. The longer edges of each component that define the widths may be matched up and the shorter edges that define the heights may be matched up. The size and shape of the exterior 206 of the electric coupling 204 may also help the patient align the controller end connector with the patient adapter 180, as the exterior 206 may be sized and shaped to fit snuggly within the central lumen 198 of the controller section 186 of the patient adapter 180.

In some embodiments, the electric couplings 166 and 204 may be symmetrically positioned about at least one axis. This allows the electric couplings 166 and 204 to be coupled in multiple orientations, such as with one of the couplings being rotated 180° relative to another. In some embodiments, the symmetry may be about two or more axes, which may allow electric couplings 166 and 204 to be coupled at 90° or smaller rotational increments. The use of the shapes and sizes of the outer peripheries matching, or substantially matching, along with the use of symmetrical electric couplings, helps to eliminate the need for other alignment features, such as visual markings, distinguishing textural features, and the like. It will be appreciated that while not necessary, some embodiments may include one or more additional alignment features to further enhance the ease of use of the patient adapter 180 and the controller end connector 196.

Figure 10B:
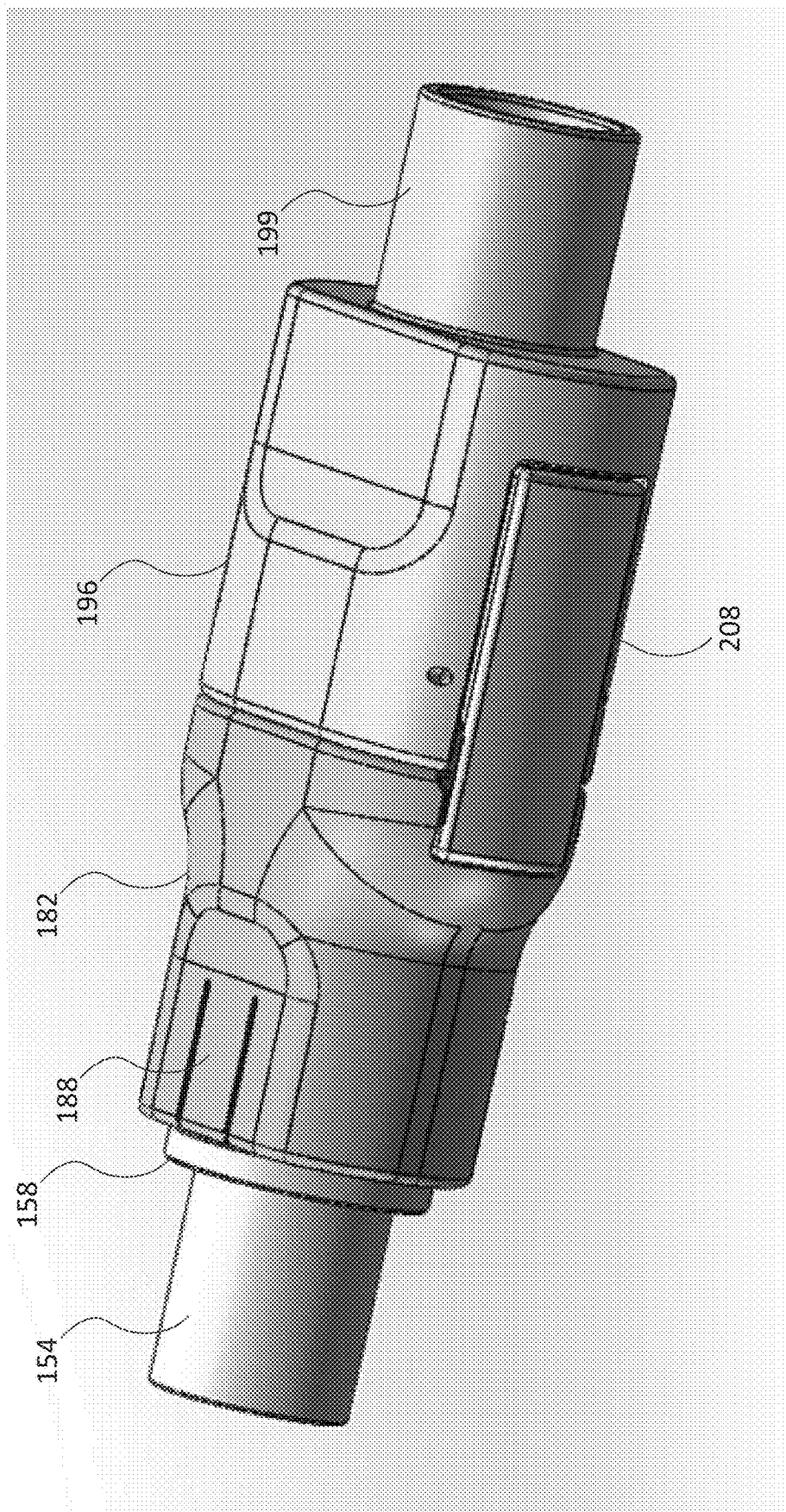
FIG. 10B is an isometric view of the driveline cable assembly of FIG. 10A in a connected configuration.

Once properly aligned with the patient adapter 180, the controller end connector 196 may be pushed against the patient adapter 180 until the pivotable arms 208 contact an exterior of the patient adapter 180 proximate the recesses 191, which causes the pivotable arms 208 to pivot outward. Once the pivotable arms 208 are pushed onto the patient adapter 180 enough to align the pivotable arms 208 with the recesses 191, the protrusions 210 will snap into the recesses 191, thereby securing the controller end connector 196 with the patient adapter 180, as shown in FIG. 10B. Here, the outer peripheries of the controller section 186 of the patient adapter 180 and the controller end connector 196 are substantially the same, with the outer surfaces generally planar with one another. The adapter body 182 has a thickness that increases from the percutaneous section 184 to the controller section 186 to increase a form factor to make it easier for patient to couple the controller end connector 196 with the patient adapter 180.

Figure 10C:
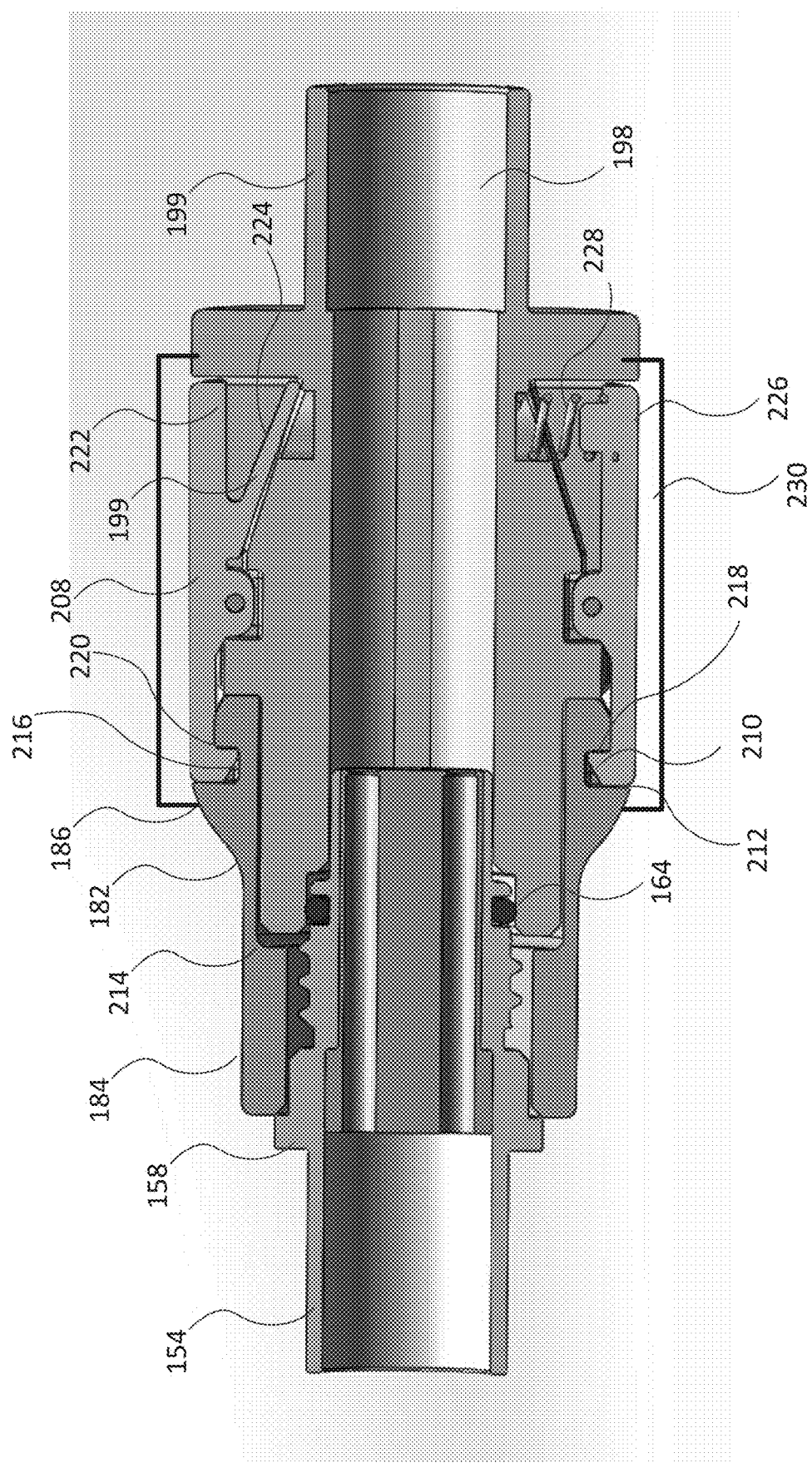
FIG. 10C is a cross-sectional view of the driveline cable assembly of FIG. 10A in a connected configuration.

As shown in FIG. 10C, the central lumen 198 of the patient adapter 180 receives both the external portion 156 of the percutaneous end connector 150 and the adapter portion 200 of the controller end connector 196. The electric couplings 166 and 204 of the respective connectors 150 and 196 may engage with one another, allowing the controller 20 to interact with the left ventricle assist device 14 using the fully connected driveline cable 152. In some embodiments, the sealing element 164 may be a radial annularly shaped seal that protects the interface between the external portion 156 of the percutaneous end connector 150 and the adapter portion 200 of the controller end connector 196 For example, a distal end 212 of the adapter portion 200 may be positioned over the external portion 156 of the percutaneous end connector 150 and contact the sealing element 164 to seal the interior of the interface and prevent dirt, water, and/or other environmental contaminants from reaching the interface between the electric couplings 166 and 204. To accommodate a larger exterior 206 of the electric coupling 204, the central lumen 198 of the patient adapter 180 may widen at a shoulder 214. When fully inserted, the distal end 212 of the adapter portion 200 may be positioned adjacent the shoulder 214 to set a maximum insertion depth. The narrower portion of the central lumen 198 may snuggly accommodate the exterior portion of the percutaneous end connector 150. For example, the narrower portion may have a diameter of no greater than about 0.5 inches (oftentimes noticeably smaller) to accommodate a similarly sized percutaneous end connector 150.

In some embodiments, the peripheral shape of the central opening may vary. For example, the narrower portion that receives the external portion 156 of the percutaneous end connector 150 may be generally circular in shape to receive a circular external portion 156. The wider portion may be generally stadium shaped (or other non-circular shape) to receive a different shaped exterior 206 of the electric coupling 204. This allows a circular percutaneous end connector 150 to be used, while taking advantage of alignment benefits provided by a non-circular exterior 206. This design makes boring the internal cavity within the patient's abdomen easier, while minimizing the size of the hole needed.

In some embodiments, the protrusion 210 of the pivotable arm 208 may be configured to be inserted within the recess 191 formed in the adapter body 182. A distal surface 216 of the protrusion 210 may be beveled. During installation of the controller end connector 196, the distal surface 216 may contact an exterior surface of the controller section 186 of the patient adapter 180, which may cause the pivotable arm 208 to deflect outward until the protrusion 210 is aligned with the recess 191. The protrusion 210 may then snap into the recess 191, causing a proximal surface 218 of the protrusion 210 to slide against a proximal side wall 220 of the recess 191. Oftentimes, the proximal side wall 220 may extend from an outer surface of the patient adapter 180 at an angle of no less than 90°. Such design helps ensure that the protrusion 210 stays engaged within the recess 191 at all times, including when subjected to pulling forces along the longitudinal axis of the controller end connector 196.

At times the patient may need to disconnect the controller end connector 196 from the patient adapter 180 for various reasons, such as for showering, swimming, and/or controller replacement. To facilitate such removal, the pivotable arms 208 may be configured to be easily pivoted outward so as to disengage the protrusions 210 from the recesses 191. As just one example, each pivotable arm 208 may be formed with an integrated spring mechanism 222. In such embodiments, an extension 224 may protrude at an angle from a main body of the pivotable arm 208 such that the extension 224 contacts a wall of an angled channel formed within the controller end connector 196. The patient may push down on a proximal end 226 of the pivotable arm 208, causing the proximal end 226 and/or the extension 224 to bend toward one another, drawing the protrusion 210 out of engagement with the recess 191. In other embodiments, the pivotal arm 208 may be used in conjunction with a compression spring 228. In such embodiments, the proximal end 226 may be coupled with the compression spring 228, which may be positioned within a body of the controller end connector 196. The compression spring 228 may bias the pivotable arm 208 toward an engaged state. To remove the controller end connector 196, a patient may press against the proximal end 226, thereby compressing the spring 228 and causing the protrusion 210 to disengage from the recess 191.

In some embodiments, a sleeve 230 may be slid around all or part of the patient adapter 180 and/or the controller end connector 196. Sleeve 230 ensures that the latches or protrusions 210 are not accidentally disengaged. Sleeve 230 may be a flexible or rigid material that is designed to fit around at least a portion of the arms 208 to prevent protrusions 210 from being released from recesses 191. The sleeve 230 may be slid on and off of the driveline connector assembly by the patient to either cover or expose the patient connections.

FIGS. 11A-11E depict another embodiment of a driveline connector assembly to couple a controller end connector and a percutaneous end connector. The assembly described in FIGS. 11A-11E operates in a generally similar manner to the assembly described in FIGS. 6A-10C above, however, the mating features and other mechanisms for coupling the various components are disposed in an interior of a patient adapter such that the couplings are all covered by the body of the patient adapter to prevent the mechanisms from being accidentally disengaged. It will be appreciated by those skilled in the art that internal and external coupling mechanisms described in the several embodiments may be swapped and/or used in combination with one another in accordance with the present invention.

Figure 11A:
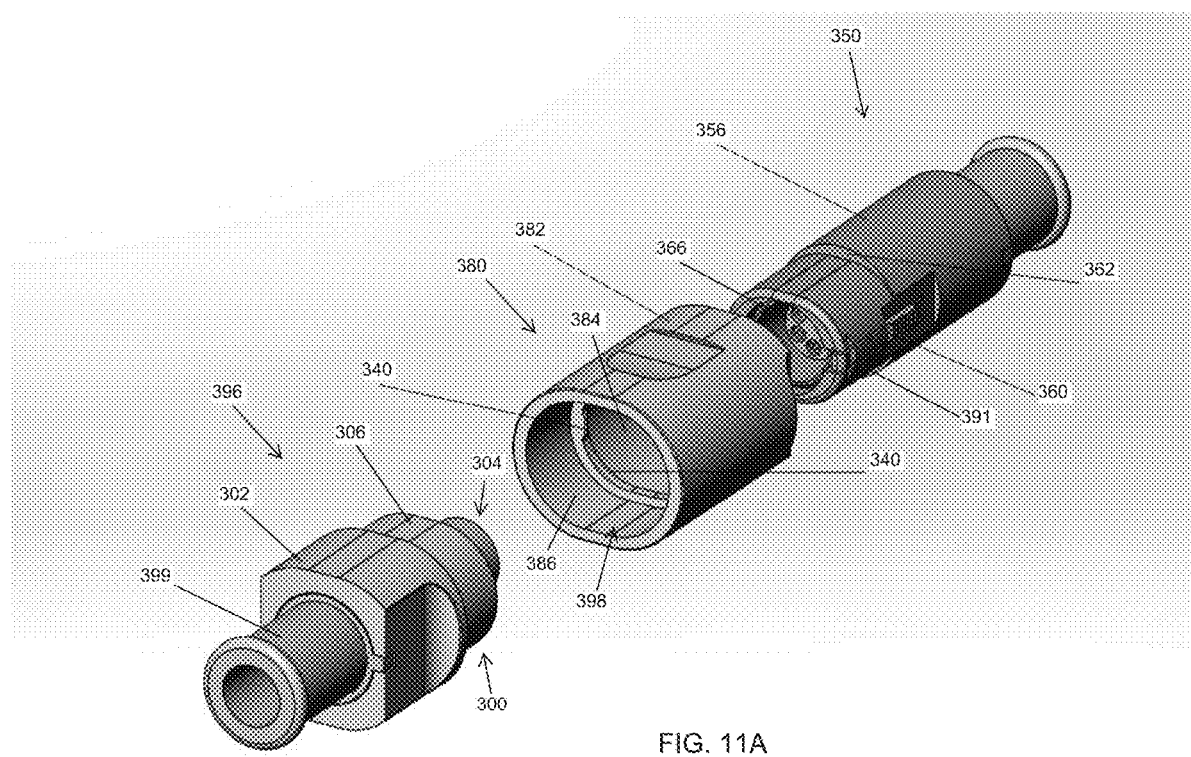
FIG. 11A is an isometric view of a driveline cable assembly in a disconnected configuration.

As shown in FIG. 11A, a percutaneous end connector 350 is coupleable with a percutaneous portion of a driveline cable, such as driveline cable 152 described above. Similar to percutaneous end connector 150, percutaneous end connector 350 is configured to be tunneled through the wall of the patient's abdomen. As such, it is desirable for the percutaneous end connector 350 to be as small as possible to help prevent infection and to as to promote quicker healing. The percutaneous end connector 350 preferably has a maximum diameter of less than about 0.50 inches, and more preferably less than about 0.40 inches. The percutaneous end connector 350 is positioned by the surgeon so that a portion of the percutaneous end connector 350 is contained within an internal cavity formed in the chest. The percutaneous end connector 350 may include an internal portion configured to receive one end of the interior or percutaneous portion 26 of driveline cable 152, with the other end of the percutaneous portion 26 being coupled with the blood pump 14. The internal portion of the percutaneous end connector 350 may be positioned within the internal cavity or incision made in the abdomen. The percutaneous end connector 350 may also include an external portion 356 configured to extend out of the internal cavity of the patient's abdomen.

Figure 11B:
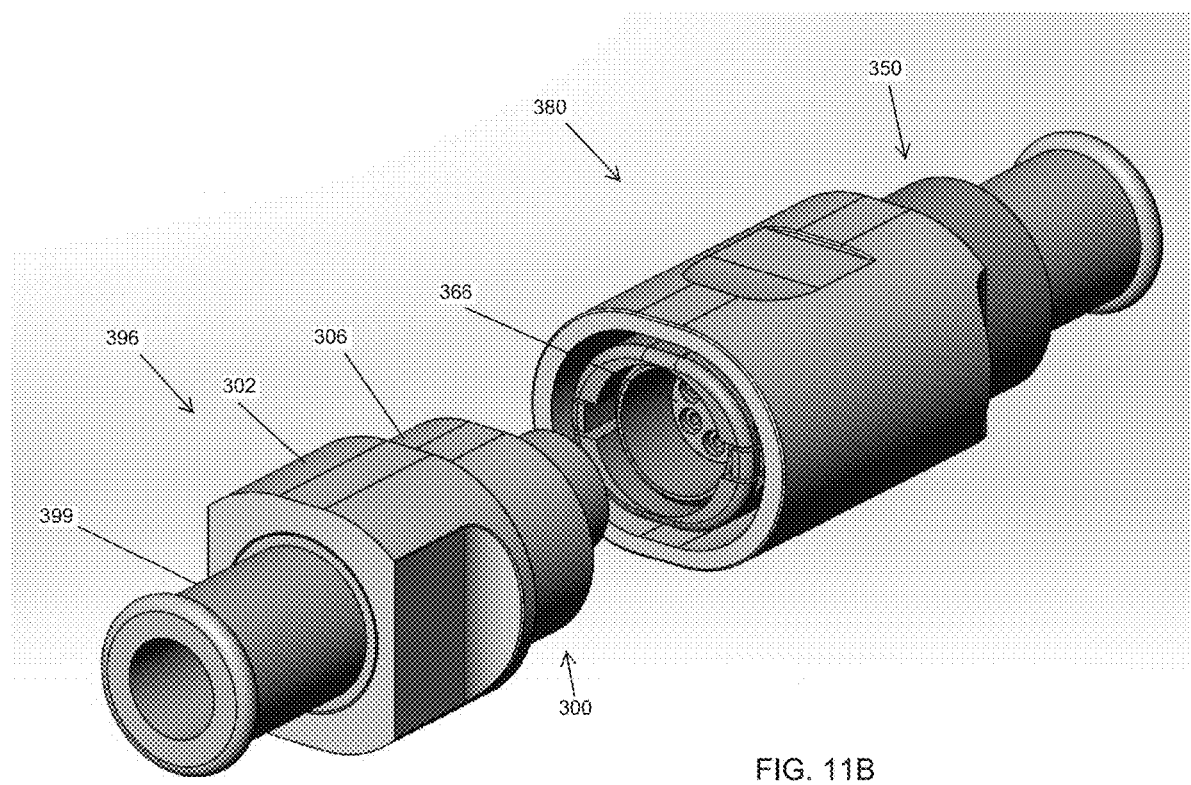
FIG. 11B is an isometric view of the driveline cable assembly of FIG. 11A in a partially connected configuration.

The external portion 356 may define a first mating feature that enables the percutaneous end connector 350 to be secured to a patient adapter 380. For example, the first mating feature may define at least one recess 360 formed in an exterior surface of the external portion 356. In some embodiments, one continuous recess may be positioned all around 360° of external surface 356. In some embodiments, one or more recesses 360 may be positioned in specific sectors of the external surface 356. For example, a top surface and a bottom surface of the external portion 356 may each include a recess 360. The recesses 360 may each be configured to receive and secure a protrusion 390 or other mating feature formed within an interior of a patient adaptor 380 as seen in FIG. 11D. In some embodiments, a distal surface of the protrusion 390 may be beveled such that the protrusion 390 may slide past any other mating features formed on an exterior surface of the external portion 356, such as recesses 391, that are used to secure a controller end connector 396 with the percutaneous end connector 350. Once the protrusion 390 is aligned with the recess 360, the protrusion 390 may then snap into the recess 360, causing a proximal surface of the protrusion 390 to slide against a proximal side wall of the recess 360. Oftentimes, the proximal side wall may extend from an outer surface of the external portion 356 of the percutaneous end connector 350 at an angle of no less than 90°. Such design helps ensure that the protrusion 390 stays engaged within the recess 360 at all times, including when subjected to pulling forces along the longitudinal axis of the patient adapter 380.

The external portion 356 may also include a second mating feature that is configured to engage with a corresponding feature of a tunneling element (not shown) and/or to further set a relative position between the percutaneous end connector 350 and the patient adapter 380. For example, the second mating feature may include a flange or stop 362 that protrudes outward from the outer surface of the external portion 356. Stop 362 may contact a portion of the tunneling element and prevent the tunneling element from sliding relative to the percutaneous end connector 350 beyond the stop 362, although it will be appreciated that other coupling mechanisms may be used to couple the percutaneous end connector 350 with a tunneling element. In some embodiments, after the tunneling element is removed, the stop 362 may be used to limit an insertion depth of the percutaneous end connector 350 within the patient adapter 380. For example, stop 362 may contact a corresponding protrusion or stop 340 formed within an interior of the patient adapter 380.

The external portion 356 of the percutaneous end connector 350 may also include an electric coupling 366 that allows the percutaneous portion 26 of the driveline cable 152 to be electrically coupled with an external portion 155 of the driveline cable 152. The electric coupling 366 may include a number of pins and/or a number of receptacles to receive pins. In some embodiments, the pins and/or receptacles of the electric coupling 366 may be arranged in a symmetric pattern, thereby allowing a user to connect the electric coupling 366 to a corresponding electric coupling 304 on a controller end connector 396 in multiple orientations. In some embodiments, the percutaneous end connector 350 may have a generally circular outer periphery, which allows a symmetrical tunneling element to be used to bore the internal cavity in the patient's abdomen. While shown here having a distal end of the external portion 356 (which is proximate the electric coupling 366) that has a non-circular outer periphery, it will be appreciated that other shapes may be used.

As the percutaneous end connector 350 has a fairly small profile (having a diameter of no more than about 0.5 inches), the patient adapter 380 is designed to be coupled with the percutaneous end connector 350 by a member of the surgical staff. The patient adapter 380 increases a form factor of the small percutaneous end connector 350 to provide a component that is easier to grip and manipulate for older and/or less dexterous patients to handle. For example, the form factor may be defined by the outer periphery of the various sections of the patient adapter. At least one major dimension (width and/or height) of the outer periphery may have a minimum thickness that is sufficiently large so as to be easily grasped and manipulated by patients who lack dexterity and/or clear vision. For example, to help patients more easily handle the patient adapter 380 the adapter 380 may have an adapter body 382 that has a maximum thickness of at least 0.75 inches. In some embodiments, all or a substantial portion of the adapter body 382 may have the maximum thickness, while in other embodiments only half or a smaller portion of the adapter body 382 has the maximum thickness.

The adapter body 382 has a percutaneous section 384 that is positioned at one end of the adapter body 382 and a controller section 386 that is positioned at the opposite end of the adapter body 382. The adapter body 382 defines a central lumen 398 that extends through an entire length of the adapter body 382 and may receive the electric coupling 366 of the percutaneous end connector 350 and an electric coupling 304 of the controller end connector 396. For example, a portion of the central lumen 398 that is positioned within the percutaneous section 384 may be configured to receive an end of the percutaneous end connector 350, while a portion of the central lumen 398 that is positioned within the controller section 386 may be configured to receive an end of the controller end connector 396.

In some embodiments, the percutaneous section 384 may include an interior mating feature that is configured to engage a corresponding mating feature of the percutaneous end connector 350 so as to secure the percutaneous end connector 350 with the patient adapter 380. For example, as seen in FIG. 11D, the mating feature of the percutaneous section 384 may include the at least one protrusion 390 formed on an interior surface of the adapter body 382, within central lumen 398, such that the protrusion extends inward into an open interior of the patient adapter 380. The protrusion 390 may be inserted within the recess 360 of the percutaneous end connector 350. Once the percutaneous end connector 350 is fully inserted within the patient adapter 380, a stop 340 of the patient adapter 380 may be positioned against the flange or stop 362, generally sealing the interior of the connection and setting a maximum depth of insertion of the percutaneous end connector 350 within the patient adapter 380 as shown in FIG. 11B.

Turning back to FIG. 11A, the external portion 356 of the percutaneous end connector 350 may include a second mating feature configured to releasably engage a corresponding mating or engagement feature of a controller end connector 396 so as to secure the controller end connector 396 to the percutaneous end connector 350 within the patient adapter 380. For example, the second mating feature may include at least one recess 391 formed in an exterior surface of the external portion 356. In some embodiments, a recess 391 or other mating feature may be provided on opposite surfaces of the external portion 356. For example, a first side and a second side of the external portion 356 may each include at least one recess 391. The recesses 391 may each be configured to receive a protrusion 310 formed on an interior portion of the controller end connector 396 as shown in FIG. 11D. In some embodiments, the first mating feature and the second mating feature are positioned on different, adjacent sides of the adapter body 382. For example, the first mating feature may be formed on or coupled with the top and/or bottom of the adapter body 382, while the second mating feature may be formed on or coupled with a first side and/or a second side of the adapter body 382.

Oftentimes, the adapter body 382 has a non-circular cross-sectional shape, and oftentimes a shape that has sides that are distinguishable using touch alone. For example, the adapter body 382 may have a cross-sectional shape of a rectangle with rounded corners. Such a cross-section allows a user to identify a proper orientation of the adapter body 382 when attempting to align and connect the adapter body 382 with the controller end connector 396. Such cross-sections also eliminate the need for different textures and/or alignment features to help patients align the components to ensure that the electric couplings 366 and 304 may be properly engaged. However, in some embodiments, such differing textures, markings, and/or other alignment aids may be included to further contribute to the ease of connection. As shown in FIG. 11B, once coupled together by surgical staff, the percutaneous end connector 350 and the patient adapter 380 are typically not disengaged from one another, as that would require surgical staff to perform another coupling process. As such, it is important that the mating features or other securement mechanisms are designed to maintain a permanent (or semi-permanent) connection.

Turning back to FIG. 11A, controller end connector 396 may include a controller portion 399 and an adapter portion 300 separated by a medial portion 302. The controller portion 399 may be configured to receive a first end of the external portion 155 of the driveline cable 152, with the other end of the external portion 155 of the driveline cable 152 being coupled with the controller 20. The adapter portion 300 may include electronic coupling 304 that is configured to interface with the electric coupling 366 of the percutaneous end connector 350. For example, the electronic coupling 304 may include one or more pins 346 as seen in FIG. 11E or other electric connectors that may interface with the corresponding features of the electric coupling 366. Any pins 346 or other electronic connections may include PEEK insulation. The electric coupling 304 also includes an exterior 306 that is configured to be inserted within the central lumen 398 of the patient adapter 380. The exterior 306 may be sized and shaped to fit snuggly within the central lumen 398. An interior of the adapter portion 300 may also include an engagement mechanism that may interface with the second mating feature of the percutaneous end connector 350. For example, the engagement mechanism may include at least one protrusion 310. Protrusion 310 may have a hook-like shape that engages a peripheral side wall of the recess 391, which may be at an angle less than 90° relative to the external portion 356 of the percutaneous end connector 350, thereby forming a latch that is heavily resistant to lateral forces. When interfaced with the percutaneous end connector 350, the exterior 306 of the controller end connector 396 is disposed within the central lumen 398 between the controller section 386 of the patient adapter 380 and a body of the percutaneous end connector 350. In some embodiments, the portion of the central lumen 398 formed in the controller section 386 may act as a second mating feature that engages the exterior 306 to secure the exterior 306 within the central lumen 398, such as using a press fit, friction fit, or similar connection. In some embodiments, the connection between the percutaneous end connector 350, the patient adapter 380, and the controller end connector 396 may be secured by 1) the interface between the recess 360 and the protrusion 390, 2) the interface between flange or stop 362 and stop 340, 3) the interface between the recess 391 and protrusion 310, 4) the interface between electric couplings 366 and 304, and/or 5) the interface between the central lumen 398 and exterior 306.

FIG. 11B depicts the connection a patient must make between the controller end connector 396 and the patient adapter 380. Here, the patient adapter 380 is already coupled with the percutaneous end connector 350. Such a connection is often made by the surgical staff during the implantation process. The coupling of the controller end connector 396 and the patient adapter 380 is made easier for the patient by the larger form factor provided by the greater thicknesses of both components. The alignment of the controller end connector 396 and the patient adapter 380 may be simplified by the outer peripheries of at least a portion of both components having substantially the same cross-sectional size and shape. Oftentimes, the outer peripheries will be shaped to have one side or pair of sides that are different than the others. For example, rectangular or stadium shapes may be used as the longer sides of each component may be aligned with one another to help align electric coupling 304 within the central lumen 398 of the patient adapter 380. For example, the adapter body 382 and/or controller end connector 396 may have widths that are greater than their heights. The longer edges of each component that define the widths may be matched up and the shorter edges that define the heights may be matched up. Having different dimensions along different sides of the adapter body 382 and/or the controller end connector 396 provide a tactile feel that a user may rely on to properly align the components. The size and shape of the exterior 306 of the electric coupling 304 may also help the patient align the controller end connector with the patient adapter 380, as the exterior 306 may be sized and shaped to fit snuggly within the central lumen 398 of the controller section 386 of the patient adapter 380.

In some embodiments, the electric couplings 366 and 304 may be symmetrically positioned about at least one axis. This allows the electric couplings 366 and 304 to be coupled in multiple orientations, such as with one of the couplings being rotated 180° relative to another. In some embodiments, the symmetry may be about two or more axes, which may allow electric couplings 366 and 304 to be coupled at 90° or smaller rotational increments. The use of the shapes and sizes of the outer peripheries matching, or substantially matching, along with the use of symmetrical electric couplings, helps to eliminate the need for other alignment features, such as visual markings, distinguishing textural features, and the like. It will be appreciated that while not necessary, some embodiments may include one or more additional alignment features to further enhance the ease of use of the patient adapter 380 and the controller end connector 396.

Figure 11C:
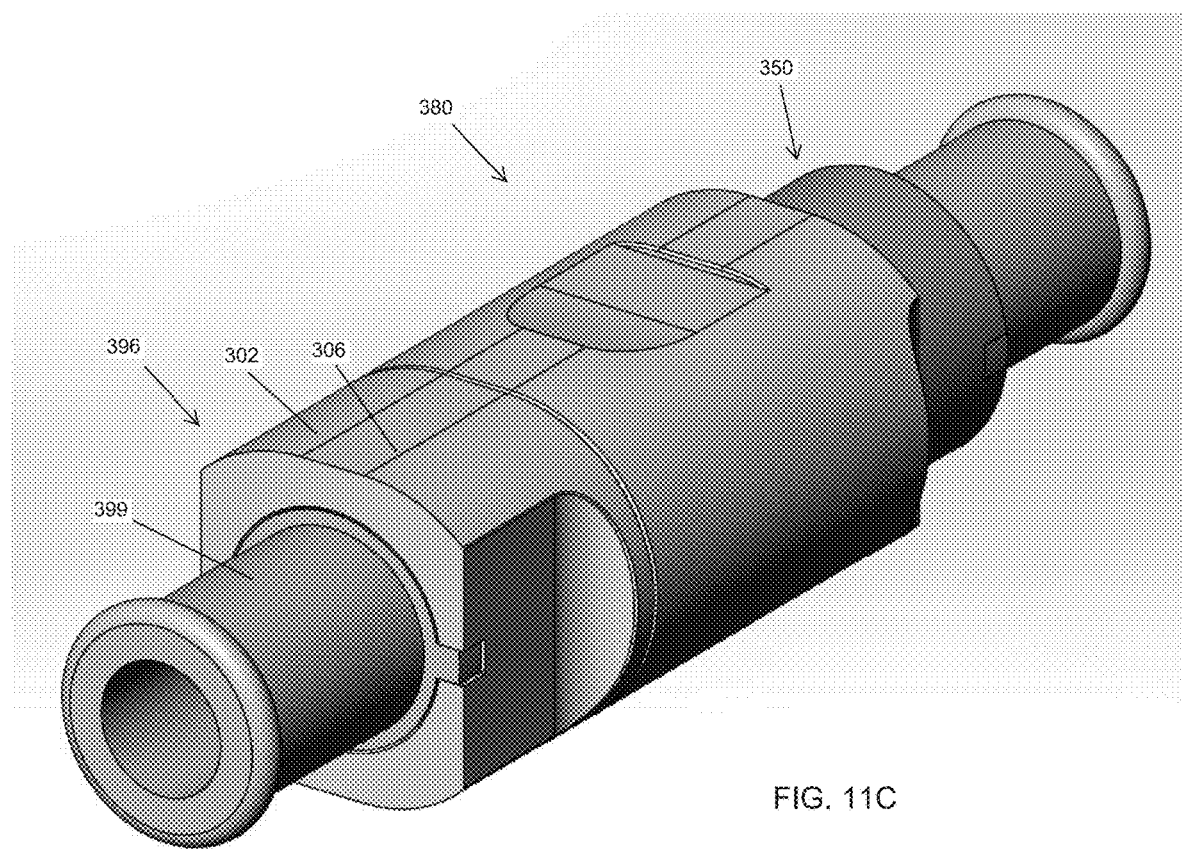
FIG. 11C is an isometric view of the driveline cable assembly of FIG. 11A in a connected configuration.
Figure 11D:
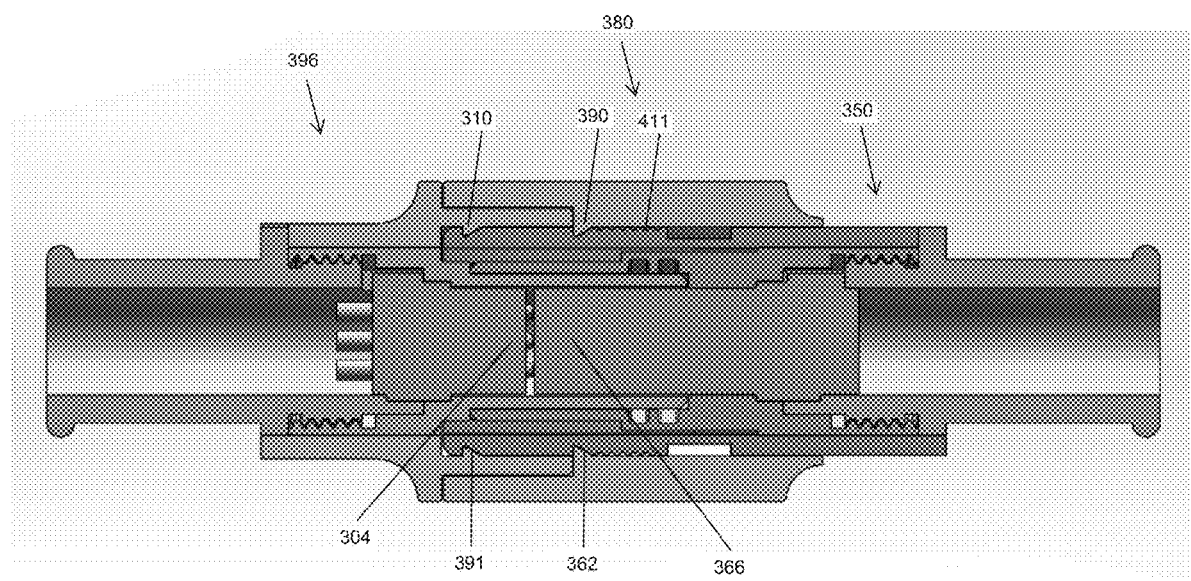
FIG. 11D is a top cross-sectional view of the driveline cable assembly of FIG. 11A in a connected configuration.
Figure 11E:
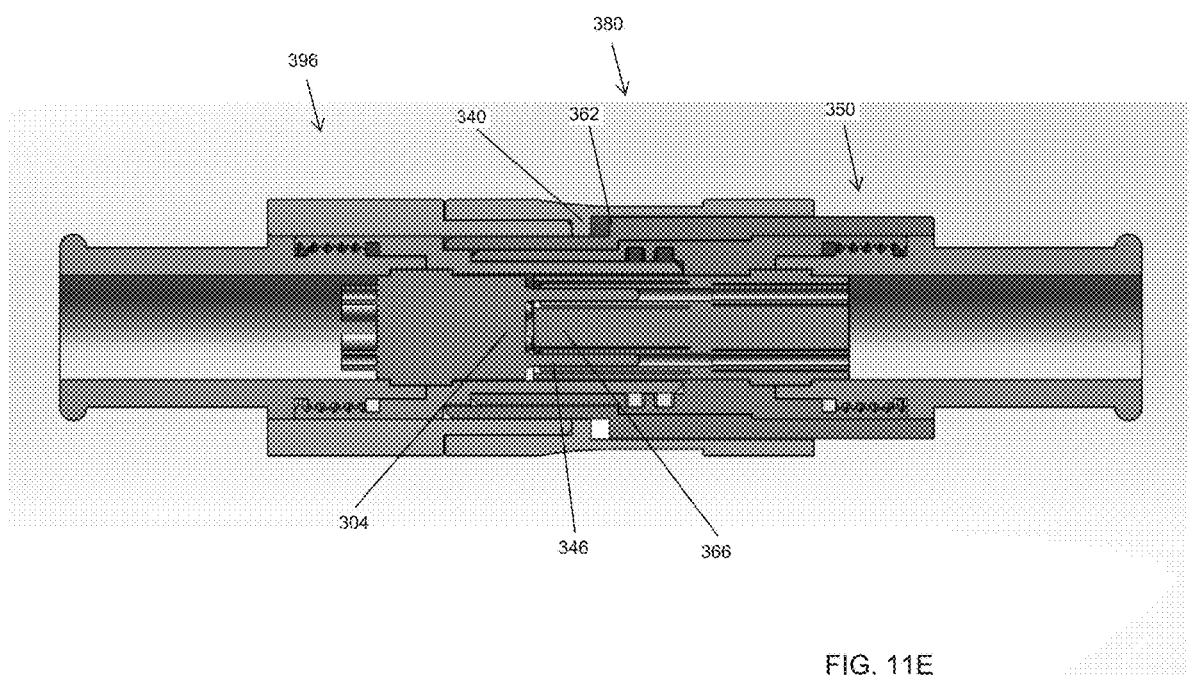
FIG. 11E is a side cross-sectional view of the driveline cable assembly of FIG. 11A in a connected configuration.

Once properly aligned with the patient adapter 380, the controller end connector 396 may be pushed against the patient adapter 380 until 1) the protrusion 310 engages with recess 391, 2) the electric couplings 304 and 366 engage with one another, and 3) a distal end of the exterior 306 contacts the stop 340 as shown in FIGS. 11C-11E. Here, the outer peripheries of the controller section 386 of the patient adapter 380 and the controller end connector 396 are substantially the same, with the outer surfaces generally planar with one another.

The central lumen 398 of the patient adapter 380 receives both the exterior portion 356 of the percutaneous end connector 350 and the adapter portion 300 of the controller end connector 396. The electric couplings 366 and 304 of the respective connectors 350 and 396 may engage with one another, allowing the controller 20 to interact with the left ventricle assist device 14 using the fully connected driveline cable 152. In some embodiments, one or more sealing elements may be provided that protect the interface between the exterior portion 356 of the percutaneous end connector 350 and the adapter portion 300 of the controller end connector 396.

In some embodiments, the peripheral shape of the central opening may vary. For example, the portion of the central lumen 398 that receives the exterior portion 356 of the percutaneous end connector 350 may be generally circular in shape to receive a circular exterior portion 356. The portion of the central lumen 398 that receives the controller end connector 396 may be generally stadium shaped (or other non-circular shape) to receive a different shaped exterior 306 of the electric coupling 304. This allows a circular percutaneous end connector 350 to be used, while taking advantage of alignment benefits provided by a non-circular exterior 306. This design makes boring the internal cavity within the patient's abdomen easier, while minimizing the size of the hole needed.

Figure 11F:
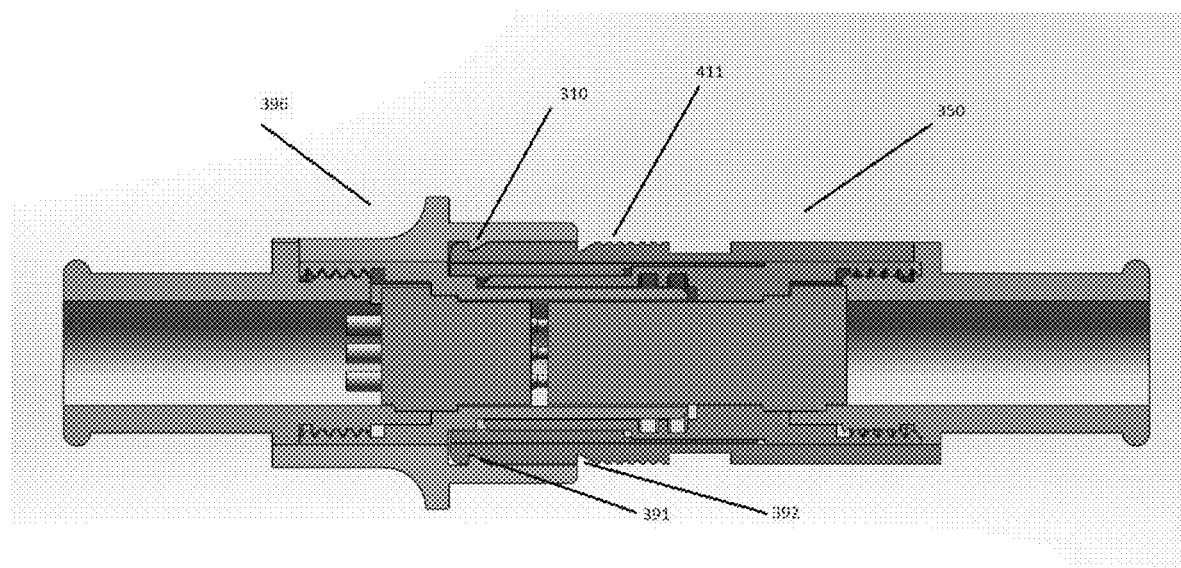
FIG. 11F is a top cross-sectional view of the driveline cable assembly of FIG. 11A in a partially connected configuration.

It is required to test LVAD functionality during manufacturing and, in some instances, prior to LVAD implantation. Therefore, multiple connection and disconnection of percutaneous end connector 350 and controller end connector 396 must be performed before patient adapter 380 is installed onto percutaneous end connector 350. FIG. 11F depicts such a connection. In this case, disconnection is performed with actuators or buttons 411. When connected, protrusion 310 of controller end connector 396 engages recess 391 of percutaneous end connector 350 to secure connection. To disconnect, operator presses buttons 411 releasing recesses 391 from protrusion 310 and disconnecting percutaneous end connector 350 from controller end connector 396. In the illustrated embodiment, two buttons 411 are positioned on the opposite sides of percutaneous end connector 350, and simultaneous engagement of these buttons by two fingers is required for disconnection. This requirement provides additional safety to prevent accidental disconnection. In other embodiments, a special tool that provides pincer motion may be used to replace buttons 411 and release recesses 391 from protrusion 310.

Buttons 411 on percutaneous end connector 350 may also be used to release percutaneous end connector 350 from the tunneling element (not shown). In this case, the mating feature in the tunneling element may be similar to protrusion 310 and it is engages recess 391 of percutaneous end connector 350 prior to tunneling procedure. Following the tunneling, surgeon presses buttons 411 to release recesses 391 from protrusion in tunneling element.

The various components of the driveline cable assemblies disclosed herein may be formed of resilient, corrosion-resistant materials. For example, metal alloys, such as those including titanium and/or aluminum, as well as polymers may be used. Oftentimes, the components placed within the body, such as the percutaneous end connectors may be formed from polymers to help prevent rejection by the body, while still providing a sturdy and long-lasting component. In some embodiments, the adapter bodies and/or controller end connectors may be over-molded with a composite material, such as a silicon material to provide a softer feel to the components and for covering up any wires or exposed metal components while still allowing any snap-fit arms to deflect.

It will be appreciated that the various mating features may be interchanged, and some embodiments, multiple forms of mating features may be provided at a single location. For example, a single component may include both recesses and latches that engage with features on another component. Additionally, one or more other mating features and fasteners than those described herein may be used. For example, threaded connectors, locking or clamping mechanisms, bayonet nut connectors (BNC), other snap fit connectors, friction fit connector, other mechanical fasteners and/or any combination thereof may be used to couple the components together. Certain considerations with each connection may be observed. For example, connections between the percutaneous end connectors 150 and the patient adapter should be permanent or semi-permanent and in some embodiments may require tools to secure the connection. Conversely, the connection between a patient adapter and a controller end connector should be releasable such that a patient may connect and disconnect the controller end connector when needed. Additionally, this connection should be easily made without the use of tools.

Figure 12:
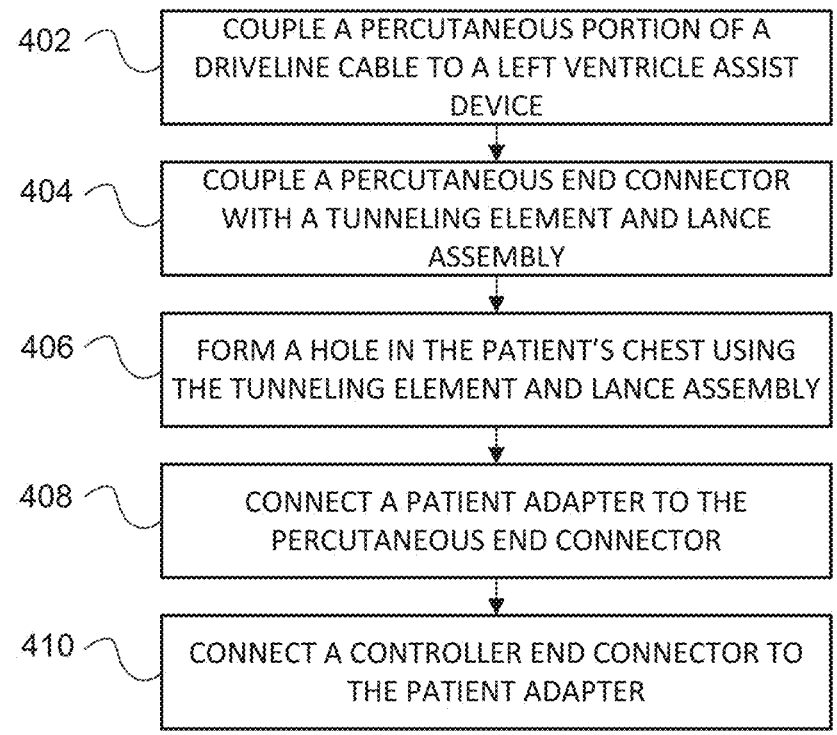
FIG. 12 is a flowchart of a process for connecting a left ventricle assist device to a controller.

FIG. 12 depicts one embodiment of a process 400 for connecting a left ventricle device to a controller. Process 400 may be performed using the systems and devices described herein. Process 400 may begin by coupling a percutaneous or internal portion of a driveline cable to a left ventricle assist device at block 402. The driveline cable may include a percutaneous end connector that is configured to extend out of the patient's chest. To help implant the percutaneous end connector, it may be coupled with a tunneling element and lance assembly at block 404. For example, a tunneling element may be screwed onto a threaded portion of the connector and/or otherwise fastened to the connector. A lance may then be threaded into and/or otherwise secured to the tunneling element. The lance may then be pushed through the patient's abdominal skin and the tunneling element may be pulled through the patient's abdominal wall at block 406. In some embodiments, the lance may be used to form a hole in the abdomen, while in other embodiments, a scalpel or other instrument may be used to form the hole, with the lance being inserted into the pre-formed hole.

Once through the abdominal wall, the tunneling element and lance may be removed, leaving an interior portion of the percutaneous cable within the abdominal wall while an exterior portion of the percutaneous cable and percutaneous end connector extend outward from the abdomen. The surgical staff may then connect a patient adapter to the small percutaneous end connector at block 408. This may involve coupling one or more snap-fit connectors or other fastening mechanisms to secure the components together. The patient adapter is configured to grow a form factor of the driveline cable assembly to increase the ease of use for patients who may have a difficulty manipulating smaller components, such as the percutaneous end connector, which should remain as small as possible for health and safety reasons.

Once the patient adapter is installed, the surgical staff and/or patient may connect a controller end connector to the patient adapter at block 410. This may involve properly aligning the controller end connector with the patient adapter and pushing the components together to engage one or more snap fit connectors. The controller end connector may be coupled with an exterior portion of the driveline cable that extends to the left ventricle assist device controller. The coupling of the controller end connector and the patient adapter creates an electrical coupling between the interior driveline cable and the exterior driveline cable, thus enabling interactions between the controller and the left ventricle assist device. To remove the controller end connector for any reasons, the patient or other person may disengage the snap-fit connectors, such as by depressing a portion of the connector to disengage a latch or other protrusion, allowing the controller end connector to be slid out of engagement with the patient adapter.

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A patient adapter for connecting a driveline cable between an implantable blood pump and a controller, the patient adapter comprising:
   an adapter body including a central lumen that extends through an entire length of the adapter body, the central lumen being configured to receive an end of a percutaneous end connector of the driveline cable and an end of a controller end connector of the driveline cable;
   a first mating feature configured to engage a corresponding feature of the percutaneous end connector; and
   a second mating feature configured to engage a corresponding feature of the controller end connector, wherein a thickness of the adapter body is greatest at a position proximate the controller end connector.

2. The patient adapter of claim 1, wherein:
   the first mating feature comprises a cantilever snap-fit arm having a protrusion; and
   the corresponding mating feature of the percutaneous end connector defines a recess configured to receive and secure the protrusion.

3. The patient adapter of claim 1, wherein:
   the corresponding feature of the controller end connector comprises a cantilever snap-fit arm having a protrusion; and
   the second mating feature defines a recess having a distal side that is configured to contact a proximal side of the of the protrusion, wherein the distal side extends inward from an outer surface of the adapter body at an angle no greater than 90°.

4. The patient adapter of claim 1, wherein:
   the adapter body has a maximum thickness of at most about 0.5 inches.

5. The patient adapter of claim 1, wherein:
   the first mating feature and the second mating feature are positioned on different, adjacent sides of the adapter body.

6. The patient adapter of claim 1, wherein:
   a width of the adapter body is greater than a height of the adapter body.

7. A patient adapter for connecting a driveline cable between an implantable blood pump and a controller, the patient adapter comprising:
   an adapter body defining a central lumen that extends through an entire length of the adapter body, the adapter body comprising:
      a percutaneous section positioned at a first end of the adapter body, wherein:
         a first portion of the central lumen that is positioned within the percutaneous section is configured to receive a percutaneous end connector of an interior driveline cable;
         the percutaneous section comprises a first mating feature configured to engage a corresponding feature of the percutaneous end connector so as to secure the percutaneous end connector with the patient adapter;

a controller section positioned at a second end of the adapter body, wherein:
  a second portion of the central lumen that is positioned within the controller section is configured to receive a controller end connector of an exterior driveline cable;
  the controller section comprises a second mating feature configured to releasably engage a corresponding feature of the controller end connector so as to secure the controller end connector with the patient adapter such that the controller end connector is electrically coupleable with the percutaneous end connector within the central lumen; and
  the controller section has a greater form factor than the percutaneous section.

8. The patient adapter of claim 7, wherein:
the portion of the central lumen that is positioned within the percutaneous section has a diameter of less than about 0.5 inches; and
the controller section has a thickness of at least about 0.75 inches.

9. The patient adapter of claim 7, wherein:
the form factor of the controller section is defined by an outer periphery of the controller section;
the form factor of the percutaneous section is defined by an outer periphery of the controller section; and
the outer periphery of the controller section comprises at least one major dimension that is at least 0.75 inches.

10. The patient adapter of claim 7, wherein:
the first mating feature comprises a cantilever snap-fit arm having a protrusion; and
the corresponding mating feature of the percutaneous end connector defines a recess configured to receive and secure the protrusion.

11. The patient adapter of claim 7, wherein:
the corresponding feature of the controller end connector comprises a snap-fit arm having a protrusion; and
the second mating feature defines a recess having a distal side that is configured to contact a proximal side of the of the protrusion, wherein the distal side extends inward from an outer surface of the adapter body at an angle no greater than 90°.

12. The patient adapter of claim 7, wherein:
the first mating feature and the second mating feature are positioned on different, adjacent sides of the adapter body.

13. A driveline connector assembly for connecting a cable between an implantable blood pump and a controller, the driveline connector assembly comprising:
  a percutaneous end connector configured to extend through an aperture in a patient's abdomen, the percutaneous end connector comprising:
    an internal portion configured to receive a first end of an interior driveline cable, wherein a second end of the interior driveline cable is configured to be coupled with the implantable blood pump; and
    an external portion configured to extend out of the aperture in the patient's abdomen, the external portion defining a first mating feature;
  a controller end connector comprising:
    a controller portion configured to receive a first end of an exterior driveline cable, wherein a second end of the exterior driveline cable is configured to be coupled with the controller; and
    a first engagement mechanism; and
  a patient adapter configured to couple the percutaneous end connector with the controller end connector, the patient adapter comprising:
    a percutaneous section configured to receive the external portion of the percutaneous end connector, wherein the percutaneous section defines a second mating feature configured to engage with the first mating feature of the external portion of the percutaneous end connector so as to secure the percutaneous end connector within the patient adapter;
    a controller section configured to receive the adapter portion of the controller end connector, wherein the controller section defines a second engagement mechanism configured to interface with the first engagement mechanism so as to releasably secure the adapter end of the controller end connector within the patient adapter.

14. The driveline connector assembly of claim 13, further comprising:
a sleeve configured to be slidably positioned around at least a portion of the first engagement mechanism, thereby preventing the first engagement mechanism from being disengaged from the second engagement feature.

15. The driveline connector assembly of claim 13, wherein:
the percutaneous end connector further comprises a second mating feature configured to engage with a corresponding feature of a tunneling mechanism that is configured to tunnel through a wall of the patient's abdomen, the tunneling mechanism comprising a face seal configured to interface with and seal a proximal end of the percutaneous end connector.

16. The driveline connector assembly of claim 13,
the portion of the central lumen that is positioned within the percutaneous section has a diameter of less than about 0.5 inches; and
the controller section has a thickness of at least about 0.75 inches.

17. The driveline connector assembly of claim 13, wherein:
the percutaneous end connector has a maximum diameter of no more than 0.5 inches.

18. The driveline connector assembly of claim 13, wherein:
the percutaneous end connector further comprises an interface seal configured to seal an interface between the percutaneous end connector and the controller end connector when coupled within the central lumen.

19. The driveline connector assembly of claim 13, wherein:
the second engagement mechanism defines a recess having a distal side that extends inward from an outer surface of the patient adapter at an angle no greater than 90°; and
the first engagement mechanism comprises a spring-biased arm having a protrusion configured to contact the distal side of the of the recess.

20. The driveline connector assembly of claim 13, wherein:
a maximum width of the patient adapter and the controller end connector is at least about 0.75 inches.

21. The driveline connector assembly of claim 13, wherein:
a shape of a portion of the controller portion matches a shape of the controller end connector.

22. The driveline connector assembly of claim 13, wherein:
- the external portion of the percutaneous end connector comprises a first electronic coupling; and
- the controller end connector comprises an adapter portion defining a second electronic coupling that is configured to interface with the first electronic coupling of the second side of the interior driveline cable connector.

23. The driveline connector assembly of claim 13, wherein:
- the percutaneous section has a greater thickness than the controller section, thereby increasing a form factor from the percutaneous end connector to the controller end connector.

* * * * *